United States Patent
Barthe et al.

(10) Patent No.: US 8,066,641 B2
(45) Date of Patent: Nov. 29, 2011

(54) METHOD AND SYSTEM FOR TREATING PHOTOAGED TISSUE

(75) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, L.L.C., Phoenix, AZ (US)

( * ) Notice: Subject to any disclaimer, the term of this patent is extended or adjusted under 35 U.S.C. 154(b) by 1014 days.

(21) Appl. No.: 11/163,150

(22) Filed: Oct. 6, 2005

(65) Prior Publication Data

US 2006/0241442 A1 Oct. 26, 2006

Related U.S. Application Data

(60) Provisional application No. 60/617,295, filed on Oct. 7, 2004.

(51) Int. Cl.
*A61B 8/00* (2006.01)

(52) U.S. Cl. .......................... 600/439; 601/2

(58) Field of Classification Search .......... 600/437–439, 600/407; 601/2–4; 606/33, 41–42; 607/101–108
See application file for complete search history.

(56) References Cited

U.S. PATENT DOCUMENTS

| | | |
|---|---|---|
| 4,372,296 A | 2/1983 | Fahim |
| 4,513,749 A | 4/1985 | Kino et al. |
| 4,528,979 A | 7/1985 | Marchenko et al. |
| 4,567,895 A | 2/1986 | Putzke |
| 4,586,512 A | 5/1986 | Do-Huu et al. |
| 4,858,613 A | 8/1989 | Fry |
| 4,875,487 A | 10/1989 | Seppi |
| 4,917,096 A | 4/1990 | Englehart et al. |
| 4,951,653 A | 8/1990 | Fry |
| 4,955,365 A | 9/1990 | Fry et al. |
| 4,976,709 A | 12/1990 | Sand |
| 5,036,855 A | 8/1991 | Fry et al. |
| 5,054,470 A | 10/1991 | Fry et al. |
| 5,115,814 A * | 5/1992 | Griffith et al. ............ 600/463 |
| 5,117,832 A | 6/1992 | Sanghvi |
| 5,143,074 A | 9/1992 | Dory |
| 5,150,711 A | 9/1992 | Dory |
| 5,156,144 A | 10/1992 | Iwasaki et al. |

(Continued)

FOREIGN PATENT DOCUMENTS

EP 1234566 8/2002

(Continued)

OTHER PUBLICATIONS

European Examination Report in related Application No. 05808908.7 dated Jun. 29, 2009.

(Continued)

*Primary Examiner* — Francis Jaworski
(74) *Attorney, Agent, or Firm* — Snell & Wilmer L.L.P.

(57) ABSTRACT

A method and system for ultrasound treatment of photoaged tissue are provided. An exemplary method and system are configured for first, ultrasound imaging of the region of interest for localization of the treatment area, second, delivery of ultrasound energy at a depth and pattern to achieve the desired therapeutic effects, and third to monitor the treatment area during and after therapy to assess the results and/or provide feedback. The exemplary treatment method and system can be configured for producing arrays of sub-millimeter and larger zones of thermal ablation to treat the epidermal, superficial dermal, mid-dermal and deep dermal components of photoaged tissue.

21 Claims, 22 Drawing Sheets

U.S. PATENT DOCUMENTS

| | | | |
|---|---|---|---|
| 5,163,421 A | 11/1992 | Bernstein et al. | |
| 5,230,334 A | 7/1993 | Klopotek | |
| 5,282,797 A | 2/1994 | Chess | |
| 5,304,169 A | 4/1994 | Sand | |
| 5,370,121 A | 12/1994 | Reichenberger et al. | |
| 5,371,483 A | 12/1994 | Bhardwaj | |
| 5,419,327 A | 5/1995 | Rohwedder et al. | |
| 5,458,596 A | 10/1995 | Lax et al. | |
| 5,492,126 A | 2/1996 | Hennige et al. | |
| 5,501,655 A | 3/1996 | Rolt et al. | |
| 5,520,188 A | 5/1996 | Hennige et al. | |
| 5,524,620 A | 6/1996 | Rosenschein et al. | |
| 5,526,815 A | 6/1996 | Granz et al. | |
| 5,558,092 A | 9/1996 | Unger | |
| 5,601,526 A | 2/1997 | Chapelon et al. | |
| 5,660,836 A | 8/1997 | Knowlton | |
| 5,665,053 A | 9/1997 | Jacobs | |
| 5,676,692 A | 10/1997 | Sanghvi et al. | |
| 5,690,608 A | 11/1997 | Watanabe et al. | |
| 5,755,753 A * | 5/1998 | Knowlton | 607/98 |
| 5,817,021 A | 10/1998 | Reichenberger et al. | |
| 5,820,564 A | 10/1998 | Slayton et al. | |
| 5,871,524 A | 2/1999 | Knowlton | |
| 5,873,902 A | 2/1999 | Sanghvi et al. | |
| 5,904,659 A | 5/1999 | Duarte et al. | |
| 5,919,219 A | 7/1999 | Knowlton | |
| 5,938,612 A | 8/1999 | Kline-Schoder | |
| 5,948,011 A | 9/1999 | Knowlton | |
| 5,968,034 A | 10/1999 | Fullmer et al. | |
| 5,984,882 A | 11/1999 | Rosenschein et al. | |
| 6,036,646 A | 3/2000 | Barthe et al. | |
| 6,039,048 A | 3/2000 | Silberg | |
| 6,049,159 A | 4/2000 | Barthe et al. | |
| 6,050,943 A | 4/2000 | Slayton et al. | |
| 6,071,239 A | 6/2000 | Cribbs et al. | |
| 6,086,580 A * | 7/2000 | Mordon et al. | 606/9 |
| 6,090,054 A | 7/2000 | Tagishi et al. | |
| 6,093,883 A | 7/2000 | Sanghvi et al. | |
| 6,113,558 A | 9/2000 | Rosenschein et al. | |
| 6,113,559 A | 9/2000 | Klopotek | |
| 6,120,452 A | 9/2000 | Barthe et al. | |
| 6,135,971 A | 10/2000 | Hutchinson et al. | |
| 6,176,840 B1 | 1/2001 | Nishimura et al. | |
| 6,183,426 B1 | 2/2001 | Akisada et al. | |
| 6,183,502 B1 | 2/2001 | Takeuchi | |
| 6,183,773 B1 | 2/2001 | Anderson | |
| 6,190,336 B1 | 2/2001 | Duarte et al. | |
| 6,213,948 B1 | 4/2001 | Barthe et al. | |
| 6,216,029 B1 | 4/2001 | Paltieli | |
| 6,241,753 B1 | 6/2001 | Knowlton | |
| 6,273,864 B1 | 8/2001 | Duarte et al. | |
| 6,311,090 B1 | 10/2001 | Knowlton | |
| 6,315,741 B1 * | 11/2001 | Martin et al. | 601/3 |
| 6,325,769 B1 * | 12/2001 | Klopotek | 601/2 |
| 6,350,276 B1 | 2/2002 | Knowlton | |
| 6,361,531 B1 | 3/2002 | Hissong et al. | |
| 6,375,672 B1 | 4/2002 | Aksan et al. | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,405,090 B1 | 6/2002 | Knowlton | |
| 6,409,720 B1 | 6/2002 | Hissong | |
| 6,413,253 B1 | 7/2002 | Koop et al. | |
| 6,413,254 B1 | 7/2002 | Hissong et al. | |
| 6,419,648 B1 | 7/2002 | Vitek et al. | |
| 6,425,912 B1 | 7/2002 | Knowlton | |
| 6,428,532 B1 | 8/2002 | Doukas et al. | |
| 6,430,446 B1 | 8/2002 | Knowlton | |
| 6,432,101 B1 | 8/2002 | Weber et al. | |
| 6,436,061 B1 | 8/2002 | Constantino | |
| 6,438,424 B1 | 8/2002 | Knowlton | |
| 6,440,071 B1 | 8/2002 | Slayton et al. | |
| 6,440,121 B1 | 8/2002 | Weber et al. | |
| 6,443,914 B1 | 9/2002 | Constantino | |
| 6,453,202 B1 | 9/2002 | Knowlton | |
| 6,461,378 B1 | 10/2002 | Knowlton | |
| 6,470,216 B1 | 10/2002 | Knowlton | |
| 6,500,121 B1 | 12/2002 | Slayton et al. | |
| 6,500,141 B1 | 12/2002 | Irion et al. | |
| 6,511,428 B1 * | 1/2003 | Azuma et al. | 600/439 |
| 6,514,244 B2 | 2/2003 | Pope et al. | |
| 6,540,679 B2 | 4/2003 | Slayton et al. | |
| 6,595,934 B1 * | 7/2003 | Hissong et al. | 601/3 |
| 6,607,498 B2 | 8/2003 | Eshel | |
| 6,623,430 B1 | 9/2003 | Slayton et al. | |
| 6,626,854 B2 | 9/2003 | Friedman et al. | |
| 6,626,855 B1 | 9/2003 | Weng et al. | |
| 6,663,627 B2 | 12/2003 | Francischelli et al. | |
| 6,685,640 B1 | 2/2004 | Fry et al. | |
| 6,692,450 B1 | 2/2004 | Coleman et al. | |
| 6,699,237 B2 | 3/2004 | Weber et al. | |
| 6,719,694 B2 | 4/2004 | Weng et al. | |
| 6,920,883 B2 | 7/2005 | Bessette et al. | |
| 6,932,771 B2 * | 8/2005 | Whitmore et al. | 600/459 |
| 6,936,046 B2 | 8/2005 | Hissong et al. | |
| 6,976,492 B2 | 12/2005 | Ingle et al. | |
| 7,006,874 B2 | 2/2006 | Knowlton et al. | |
| 7,020,528 B2 | 3/2006 | Neev | |
| 7,022,089 B2 | 4/2006 | Ooba et al. | |
| 7,063,666 B2 | 6/2006 | Weng et al. | |
| 7,094,252 B2 | 8/2006 | Koop | |
| 7,115,123 B2 | 10/2006 | Knowlton et al. | |
| 7,142,905 B2 | 11/2006 | Slayton et al. | |
| 7,189,230 B2 | 3/2007 | Knowlton | |
| 7,229,411 B2 | 6/2007 | Slayton et al. | |
| 7,258,674 B2 | 8/2007 | Cribbs et al. | |
| 7,347,855 B2 | 3/2008 | Eshel et al. | |
| 7,393,325 B2 | 7/2008 | Barthe et al. | |
| 7,491,171 B2 * | 2/2009 | Barthe et al. | 600/439 |
| 2002/0000763 A1 | 1/2002 | Jones | |
| 2002/0040199 A1 | 4/2002 | Klopotek | |
| 2002/0055702 A1 | 5/2002 | Atala et al. | |
| 2002/0082528 A1 | 6/2002 | Friedman et al. | |
| 2002/0082589 A1 | 6/2002 | Friedman et al. | |
| 2002/0161357 A1 | 10/2002 | Anderson et al. | |
| 2002/0169442 A1 | 11/2002 | Neev | |
| 2002/0193831 A1 | 12/2002 | Smith | |
| 2003/0032900 A1 | 2/2003 | Ella | |
| 2003/0036706 A1 | 2/2003 | Slayton et al. | |
| 2003/0040739 A1 | 2/2003 | Koop | |
| 2003/0050678 A1 | 3/2003 | Sierra et al. | |
| 2003/0065313 A1 | 4/2003 | Koop et al. | |
| 2003/0083536 A1 | 5/2003 | Eshel et al. | |
| 2003/0176790 A1 | 9/2003 | Slayton et al. | |
| 2003/0212351 A1 | 11/2003 | Hissong et al. | |
| 2003/0212393 A1 | 11/2003 | Knowlton et al. | |
| 2003/0216795 A1 | 11/2003 | Harth et al. | |
| 2003/0220536 A1 | 11/2003 | Hissong | |
| 2003/0220585 A1 | 11/2003 | Hissong | |
| 2003/0236487 A1 | 12/2003 | Knowlton | |
| 2004/0000316 A1 | 1/2004 | Knowlton et al. | |
| 2004/0001809 A1 | 1/2004 | Brisken et al. | |
| 2004/0002705 A1 | 1/2004 | Knowlton et al. | |
| 2004/0015106 A1 | 1/2004 | Coleman | |
| 2004/0030227 A1 | 2/2004 | Littrup et al. | |
| 2004/0039312 A1 | 2/2004 | Hillstead et al. | |
| 2004/0186535 A1 | 9/2004 | Knowlton et al. | |
| 2004/0206365 A1 | 10/2004 | Knowlton | |
| 2005/0055073 A1 | 3/2005 | Weber | |
| 2005/0154314 A1 | 7/2005 | Quistgaard | |
| 2005/0154332 A1 | 7/2005 | Zanelli et al. | |
| 2005/0187495 A1 | 8/2005 | Quistgaard et al. | |
| 2005/0256406 A1 | 11/2005 | Barthe et al. | |
| 2005/0261584 A1 | 11/2005 | Eshel et al. | |
| 2005/0267454 A1 | 12/2005 | Hissong et al. | |
| 2006/0020260 A1 * | 1/2006 | Dover et al. | 606/9 |
| 2006/0025756 A1 | 2/2006 | Francischelli et al. | |
| 2006/0058707 A1 | 3/2006 | Barthe et al. | |
| 2006/0058712 A1 * | 3/2006 | Altshuler et al. | 601/15 |
| 2006/0074313 A1 | 4/2006 | Slayton et al. | |
| 2006/0074314 A1 | 4/2006 | Slayton et al. | |
| 2006/0074355 A1 | 4/2006 | Slayton et al. | |
| 2006/0079816 A1 | 4/2006 | Barthe et al. | |
| 2006/0079868 A1 | 4/2006 | Makin et al. | |
| 2006/0084891 A1 | 4/2006 | Barthe et al. | |

| | | | |
|---|---|---|---|
| 2006/0089632 A1 | 4/2006 | Barthe et al. | |
| 2006/0089688 A1 | 4/2006 | Panescu | |
| 2006/0111744 A1 | 5/2006 | Makin et al. | |
| 2006/0116671 A1 | 6/2006 | Slayton et al. | |
| 2006/0122508 A1 | 6/2006 | Slayton et al. | |
| 2006/0122509 A1 | 6/2006 | Desilets | |
| 2006/0184071 A1 | 8/2006 | Klopotek | |
| 2006/0241440 A1 | 10/2006 | Eshel et al. | |
| 2006/0241442 A1 | 10/2006 | Barthe et al. | |
| 2006/0282691 A1 | 12/2006 | Barthe et al. | |
| 2007/0032784 A1 | 2/2007 | Gliklich et al. | |
| 2007/0055156 A1 | 3/2007 | Desilets et al. | |
| 2007/0167709 A1 | 7/2007 | Slayton et al. | |
| 2007/0208253 A1 | 9/2007 | Slayton et al. | |
| 2008/0071255 A1 | 3/2008 | Barthe et al. | |
| 2008/0086054 A1 | 4/2008 | Slayton et al. | |
| 2008/0214966 A1 | 9/2008 | Slayton et al. | |
| 2008/0221491 A1 | 9/2008 | Slayton et al. | |
| 2008/0275342 A1 | 11/2008 | Barthe et al. | |
| 2008/0281237 A1 | 11/2008 | Slayton et al. | |
| 2008/0281255 A1 | 11/2008 | Slayton et al. | |
| 2008/0294073 A1 | 11/2008 | Barthe et al. | |

FOREIGN PATENT DOCUMENTS

| | | |
|---|---|---|
| EP | 1262160 | 12/2002 |
| GB | 2113099 | 8/1983 |
| JP | 3123559 | 5/1991 |
| JP | 4089058 | 3/1992 |
| JP | 7080087 | 3/1995 |
| JP | 7222782 | 8/1995 |
| WO | WO9735518 | 10/1997 |
| WO | WO9832379 | 7/1998 |
| WO | WO9933520 | 7/1999 |
| WO | WO0015300 | 3/2000 |
| WO | WO0021612 | 4/2000 |
| WO | WO0182777 | 11/2001 |
| WO | WO0187161 | 11/2001 |
| WO | WO02092168 | 11/2002 |
| WO | WO03070105 | 8/2003 |
| WO | WO03086215 | 10/2003 |
| WO | WO03099177 | 12/2003 |
| WO | WO2006042168 | 4/2006 |
| WO | WO2006042201 | 4/2006 |

OTHER PUBLICATIONS

European Examination Report in related Application No. 05810308.6 dated Jun. 29, 2009.

* cited by examiner

METHOD AND SYSTEM FOR TREATING PHOTOAGED TISSUE

CROSS-REFERENCE TO RELATED APPLICATIONS

This application claims priority to and benefit of U.S. Provisional Application No. 60/617,295, entitled "Method and System for Treating Photoaged Tissue", and filed on Oct. 7, 2004.

FIELD OF INVENTION

The present invention relates to ultrasound therapy and imaging systems, and in particular to a method and system for treating photoaged tissue.

BACKGROUND OF INVENTION

Photoaging of human skin is a complex response due to inflammation, oxidative injury, cellular and extracellular changes induced by decades of sunlight exposure. UV wavelengths are thought to be mainly responsible. Both of the primary skin layers, epidermis and dermis, are affected. Epidermal photoaging includes pigmentary lesions called ephilides (freckles) and solar lentigines (larger pigmented spots), plus pre-cancerous clonal lesions of keratinocytes called actinic keratoses. Thermal destruction of part or all of the epidermis, the outermost cellular layer of skin about 0.1 mm thick, is an effective treatment for epidermal photoaging. For example, lasers that vaporize epidermis are highly effective in a treatment called laser resurfacing. However laser resurfacing creates a significant skin wound with risk of infection, and prolonged healing. Dermal changes of photoaging include solar elastosis (an accumulation of abnormally-formed elastin fibers in the upper reticular layer of the dermis), laxity, loss of elasticity, fine and coarse wrinkles. Laser resurfacing to a depth below the dermo-epidermal junction can be highly effective for improving dermal photoaging, through a process of stimulated wound healing. Deep chemical peels, dermabrasion and other methods of destruction of epidermis and/or dermis are also effective, and also produce a significant open skin wound with risk of infection and delayed healing.

Patterns of stimulated thermal damage to epidermis and/or dermis are also effective for treatment of photoaging. Recently, "fractional photothermolysis" using mid-infrared lasers to produce a microscopic array of thermal injury zones that include both epidermis and dermis was reported to be effective and well-tolerated for treatment of photoaging (D. Manstein et al. "Fractional Photothermolysis: a new concept for cutaneous remodeling using microscopic patterns of thermal injury." Lasers Surg Med 34:426-438, 2004). A primary advantage of fractional photothermolysis is that each zone of thermal injury is smaller than can be easily seen with the unaided eye, and surrounded by a zone of healthy tissue that initiates a rapid healing response. As described Manstein, the epidermis is stimulated to heal rapidly and without creating an open wound. The microscopic zones of thermally injured epidermis slough harmlessly from the skin surface after several days to several weeks, leaving a rejuvenated epidermis with less photoaging changes. Repeat treatments, which are well tolerated, can be performed until a desired result is obtained. The microscopic zones of thermal injury with fractional photothermolysis extend well into the dermis, as well. Dermis does not heal as rapidly as epidermis, in general. Over weeks to months following treatment, some of the abnormal dermis due to photoaging is remodeled, however, leading to improvement in laxity, wrinkles and skin texture.

Fractional photothermolysis (FP) is intrinsically limited to regions of approximately the upper 1-millimeter of skin. The basic concept of producing well-controlled arrays of thermal injury is therefore limited with fractional photothermolysis, to superficial aspects of photoaging. Aging, which also causes laxity of the skin, and photoaging involve deeper layers of the dermis. Solar elastosis can extend throughout the dermis, to approximately 3 mm deep or more. Laxity and loss of elasticity due to aging are bulk problems of the dermis.

A fundamental requirement for producing arrays of small thermal injury zones using a source of radiant energy that propagates and is absorbed within tissue, is that the source of radiant energy be capable of being adequately delivered to the tissue depth for which the array is desired. Near the skin surface, light can be used, as in fractional photothermolysis. However, light that propagates more than about 1 mm through skin has been multiplied scattered, and can no longer be focused or delivered.

SUMMARY OF INVENTION

A method and system for ultrasound treatment of photoaged tissue are provided. An exemplary method and system are configured for first, ultrasound imaging of the region of interest for localization of the treatment area, second, delivery of ultrasound energy at a depth and pattern to achieve the desired therapeutic effects, and third to monitor the treatment area during and after therapy to assess the results and/or provide feedback. The exemplary treatment method and system can be configured for producing arrays of sub-millimeter and larger zones of thermal ablation to treat the epidermal, superficial dermal, mid-dermal and deep dermal components of photoaged tissue.

In accordance with an exemplary embodiment, the treatment method and system use focused, unfocused, and/or defocused ultrasound for treatment of epidermal, superficial dermal, dermal, mid-dermal, and/or deep dermal components of photoaged tissue by adjusting the strength, depth, and/or type of focusing, energy levels and timing cadence. For example, focused ultrasound can be used to create precise arrays of microscopic thermal damage much deeper into the skin or even into subcutaneous structures. Detection of changes in the reflection of ultrasound can be used for feedback control to detect a desired effect on the tissue and used to control the exposure intensity, time, and/or position.

In accordance with an exemplary embodiment, an exemplary treatment system comprises an imaging/therapy probe, a control system and display system. The imaging/therapy probe can comprise various probe and/or transducer configurations. For example, the probe can be configured for a combined dual-mode imaging/therapy transducer, coupled or co-housed imaging/therapy transducers, a separate therapy probe and imaging probe, or a single therapy probe. The control system and display system can also comprise various configurations for controlling probe and system functionality, including for example a microprocessor with software and a plurality of input/output and communication devices, a system for controlling electronic and/or mechanical scanning and/or multiplexing of transducers, a system for power delivery, systems for monitoring, systems for sensing the spatial position of the probe and/or temporal parameters of the transducers, and systems for handling user input and recording treatment input and results, among others.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a method and system for treating photoaged tissue as described herein are merely indicative of exemplary applications for the invention. For example, the principles, features and methods discussed may be applied to any medical application. Further, various aspects of the present invention may be suitably applied to other applications.

Figure 1:
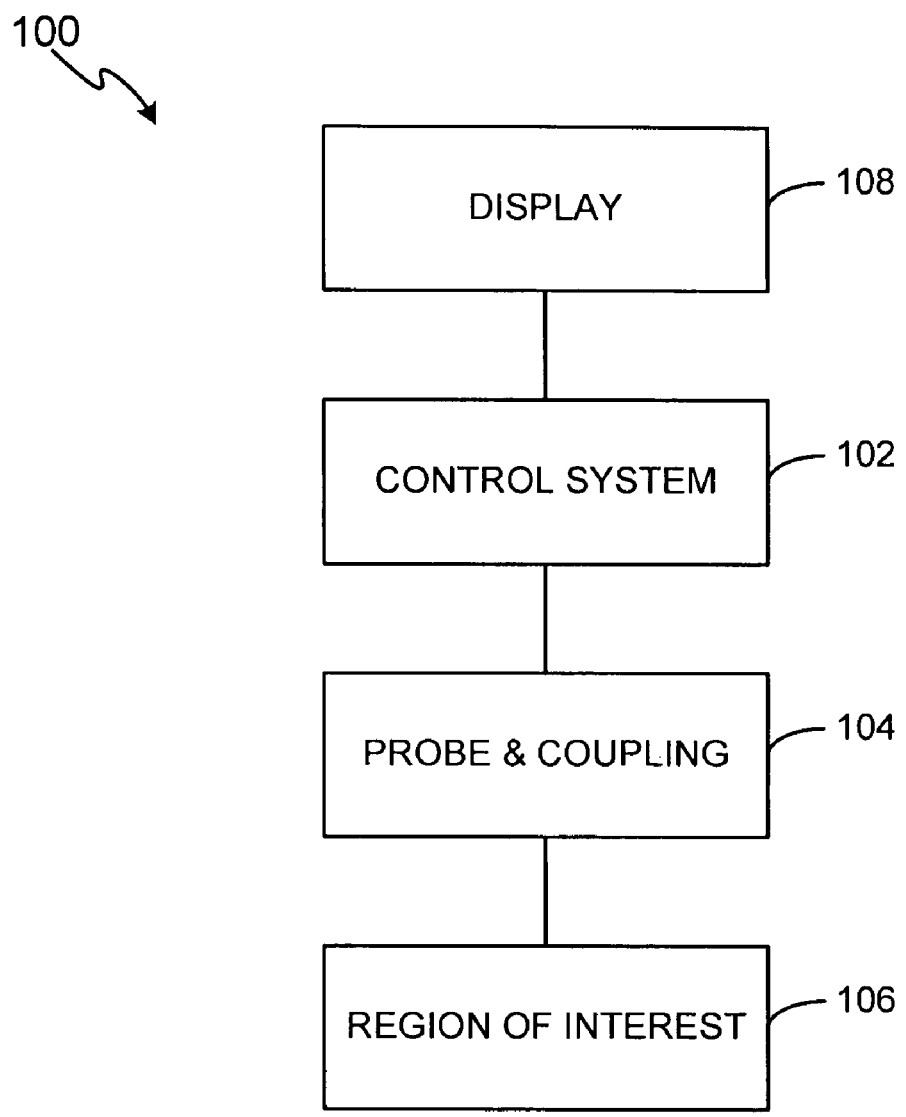
FIG. 1 illustrates a block diagram of a treatment system in accordance with an exemplary embodiment of the present invention.

In accordance with various aspects of the present invention, a method and system for treating photoaged tissue are provided. For example, in accordance with an exemplary embodiment, with reference to FIG. 1, an exemplary treatment system 100 configured to treat a region of interest (ROI) 106 comprises a control system 102, an imaging/therapy probe with acoustic coupling 104, and a display system 108. Control system 102 and display 108 can comprise various configurations for controlling functionality of probe 104 and system 100, including for example a microprocessor with software and a plurality of input/output and communication devices, a system for controlling electronic and/or mechanical scanning and/or multiplexing of transducers, a system for power delivery, systems for monitoring, systems for sensing the spatial position of the probe and/or temporal parameters of the transducers, and/or systems for handling user input and recording treatment input and results, among others. Imaging/therapy probe 104 can comprise various probe and/or transducer configurations. For example, probe 104 can be configured for a combined dual-mode imaging/therapy transducer, coupled or co-housed imaging/therapy transducers, a separate therapy probe and separate imaging probe, or a single therapy probe. In accordance with exemplary embodiments, imaging transducers may operate at frequencies from approximately 2 to 75 MHz or more, while therapy energy can be delivered at frequencies from approximately 2 to 50 MHz, with 2 MHz to 25 MHz being typical.

For the treatment of photoaged tissue, it is desirable to be able to produce well-controlled arrays of microscopic zones of thermal injury not only near the surface of skin, but in the mid-dermis, and/or in the deep dermis. Thermal ablation of dermis at temperatures greater than about 60° C., capable of producing denaturation of tissue, is also desirable in such arrays of thermal lesions. Shrinkage of dermis due to thermal action results from tightening of the skin during laser resurfacing.

In contrast to optical or RF approaches, ultrasound energy propagates as a wave with relatively little scattering, over depths up to many centimeters in tissue depending on the ultrasound frequency. The focal spot size achievable with any propagating wave energy, depends on wavelength. Ultrasound wavelength is equal to the acoustic velocity divided by the ultrasound frequency. Attenuation (absorption, mainly) of ultrasound by tissue also depends on frequency.

In accordance with an exemplary embodiment, the use of focused, unfocused, or defocused ultrasound for treatment of epidermal, superficial dermal, dermal, mid-dermal, and deep dermal components of photoaged tissue through adjustment of the strength, depth, and type of focusing, energy levels and timing cadence. For example, focused ultrasound can be used to create precise arrays of microscopic thermal ablation zones which have several advantages over fractional photothermolysis (FP). At high frequency and with superficial focusing or diffraction pattern, ultrasound ablation can mimic FP but utilize a simpler ablation device. Unlike fractional photothermolysis, ultrasound can produce an array of ablation zones much deeper into the skin or even into subcutaneous structures. Detection of changes in the reflection of ultrasound can be used for feedback control to detect a desired effect on the tissue and used to control the exposure intensity, time, and/or position.

Figure 2A:
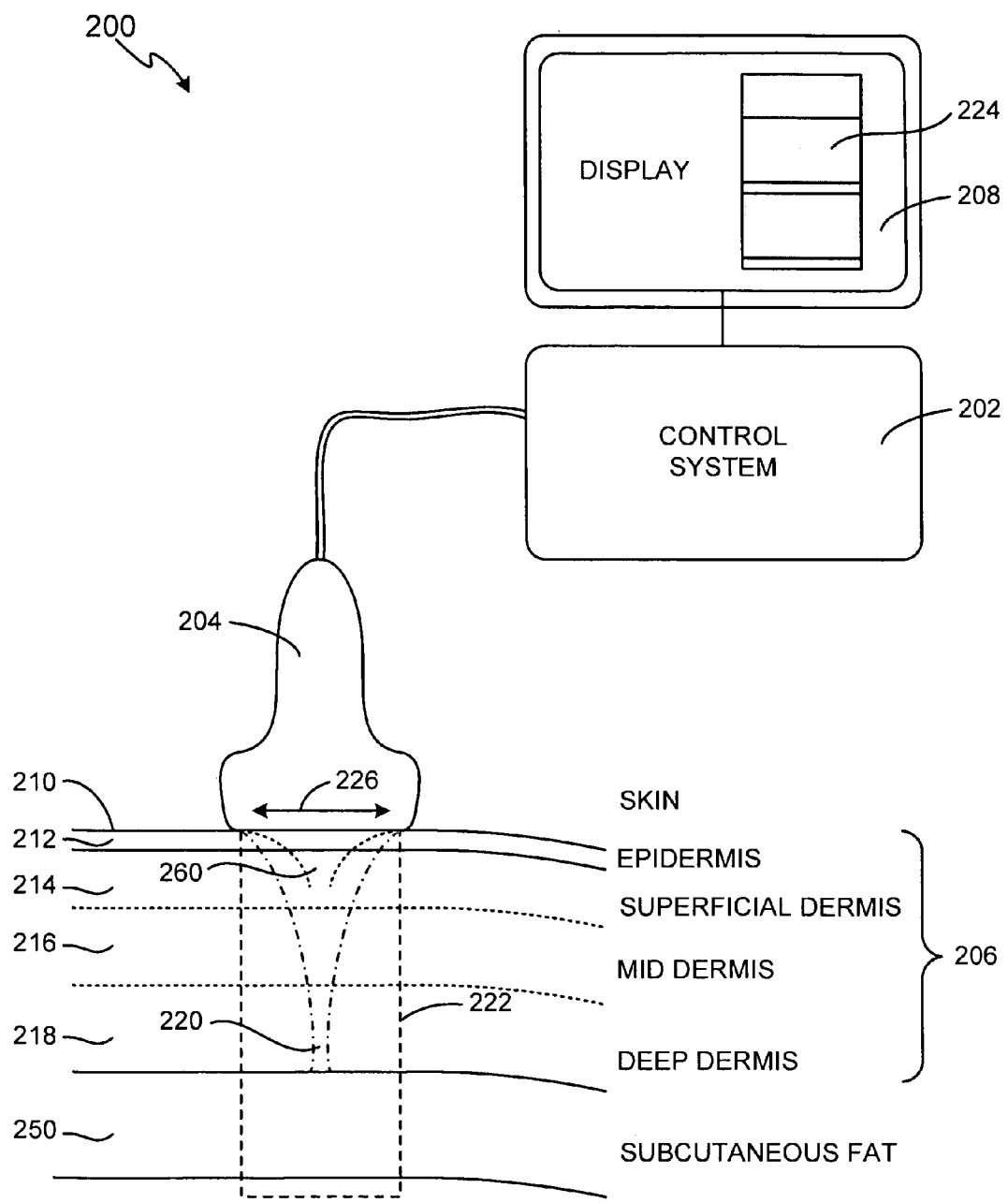
FIGS. 2A-2D illustrates a schematic diagram of an ultrasound treatment system including therapy, imaging and/or monitoring and treating photoaged tissue in accordance with various exemplary embodiments of the present invention.

To further illustrate the use of ultrasound for the treatment of photoaged tissue, with reference to FIG. 2A, an exemplary method and system are configured for initially imaging a region 222 of a region of interest 206 and displaying that region 224 during the localization of the treatment area and surrounding structures. After localization, delivery of ultrasound energy 220 at a depth, distribution, timing, and energy level to achieve the desired therapeutic effect of thermal ablation to treat an epidermis layer 212, superficial dermis layer 214, mid-dermis layer 216, and/or deep dermis layer 218 can be provided. Before, during, and after therapy, i.e., before, during, and after the delivery of ultrasound energy 220, exemplary method and system 200 can suitably monitor the treatment area and surrounding structures to plan and assess the results and/or provide feedback to control system 202 and/or a system user.

While an imaging function may be configured within control system 202 to facilitate imaging a region of interest, in accordance with another exemplary embodiment, an exemplary treatment system 200 may also be configured for therapy only or therapy and monitoring, without imaging functions. In such a case prior known depth of the region of interest, approximately 0 to 5 mm or less, is employed to achieve treatment zones in photoaged skin.

Probe 204 and/or transducers within can be mechanically and/or electronically scanned in a direction 226 to place treatment zones 260 over an extended area, such as a line to generate a matrix of closely spaced treatment spots. Treatment depth 220 can be adjusted between a range of approximately 0 to 5 mm, or otherwise until the depth of the deep dermis. Treatment may be confined to a fixed depth or a few discrete depths, or can be adjustment limited to a fine range, e.g. from approximately between 0 to 5 mm or the greatest depth of the deep dermis, or can be dynamically adjusted during treatment, to the treat region of interest 206 that lies above subcutaneous fat region 250.

Figure 2B:
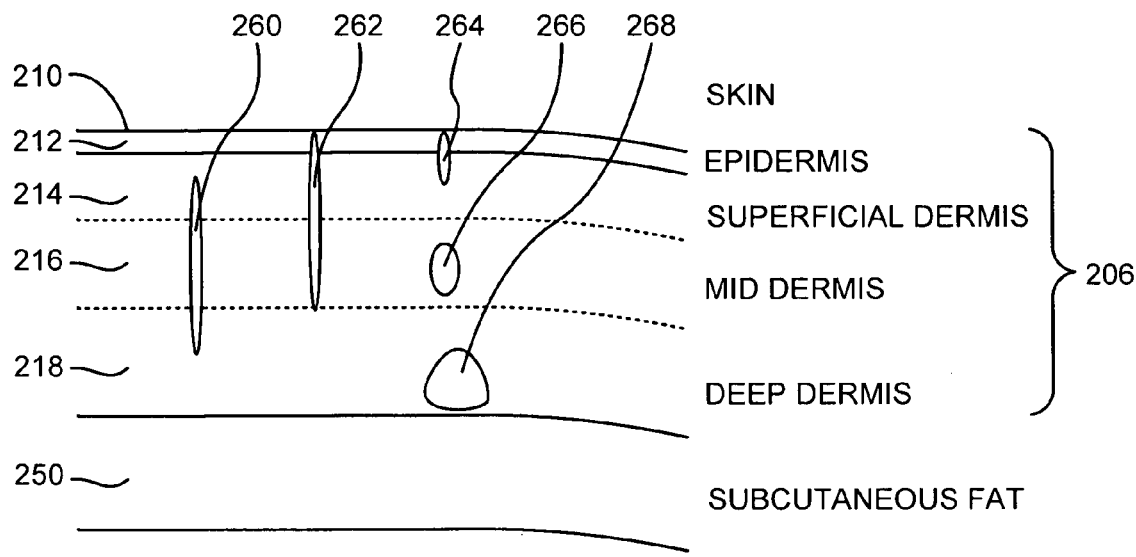

In accordance with another exemplary embodiment of the present invention, with reference to FIG. 2B, a treated zone 260 may extend throughout regions of the dermis, and may even extend to the epidermis, 262. In addition, as a treated zone increases in depth its cross section may increase from small size 264 (sub millimeter) in a shallow region near or at the epidermis, to medium size 266 (sub millimeter to millimeter sized) in a middle zone near or at the mid dermis, to large size 268 (millimeter sized) in deep zones near or at the deep dermis. Furthermore a single treated zone can have a shape expanding in cross section with depth, and/or be composed of the fusion of several smaller treatment zones. Spacing of treatment zones can be on the order of the treatment zone size. The ultrasound beam can be spatially and/or temporally controlled by changing the position of the transducer, its frequency, treatment depth, drive amplitude, and timing via the control system. For example, the ultrasound beam can be controlled as set forth in U.S. patent application Ser. No. 11/163,148, filed Oct. 6, 2005, and entitled *METHOD AND SYSTEM FOR CONTROLLED THERMAL INJURY OF HUMAN SUPERFICIAL TISSUE*, and hereby incorporated by reference.

Figure 2C:
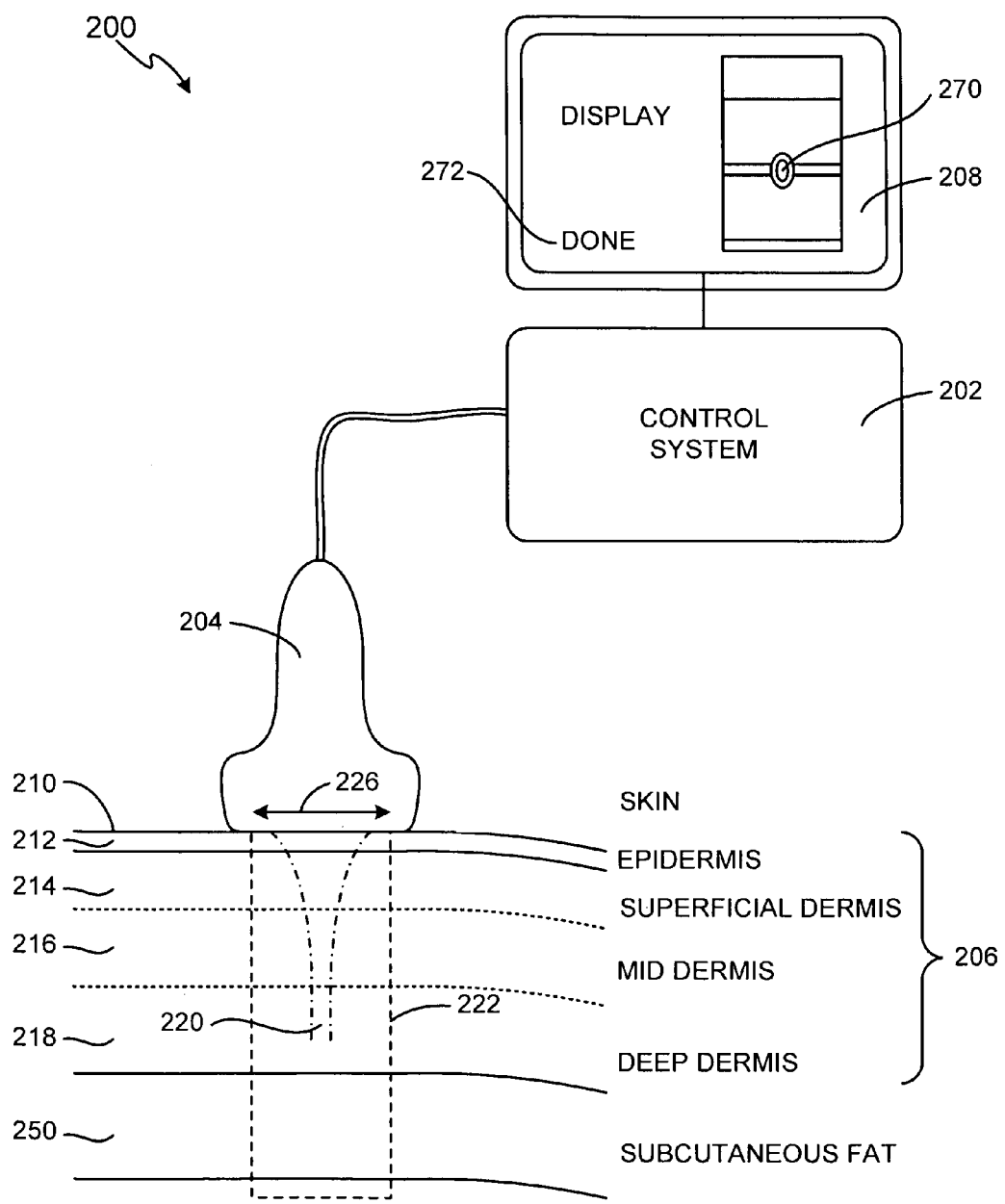

In accordance with another exemplary embodiment of the present invention, with reference to FIG. 2C, an exemplary treatment method and system 200 may be configured to monitor the temperature profile or other tissue parameters of region of interest 206, such as attenuation or speed of sound of the treatment region and suitably adjust the spatial and/or temporal characteristics and energy levels of the ultrasound therapy transducer. The results of such monitoring techniques may be indicated on display 208, such as through display of one-, two-, or three-dimensional images of monitoring results 270, or may comprise an indicator 272, such as a success, fail and/or completed/done type of indication, or combinations thereof. Additional treatment monitoring methods may be based on one or more of temperature, video, profilometry, strain imaging and/or gauges or any other suitable sensing method.

Figure 2D:
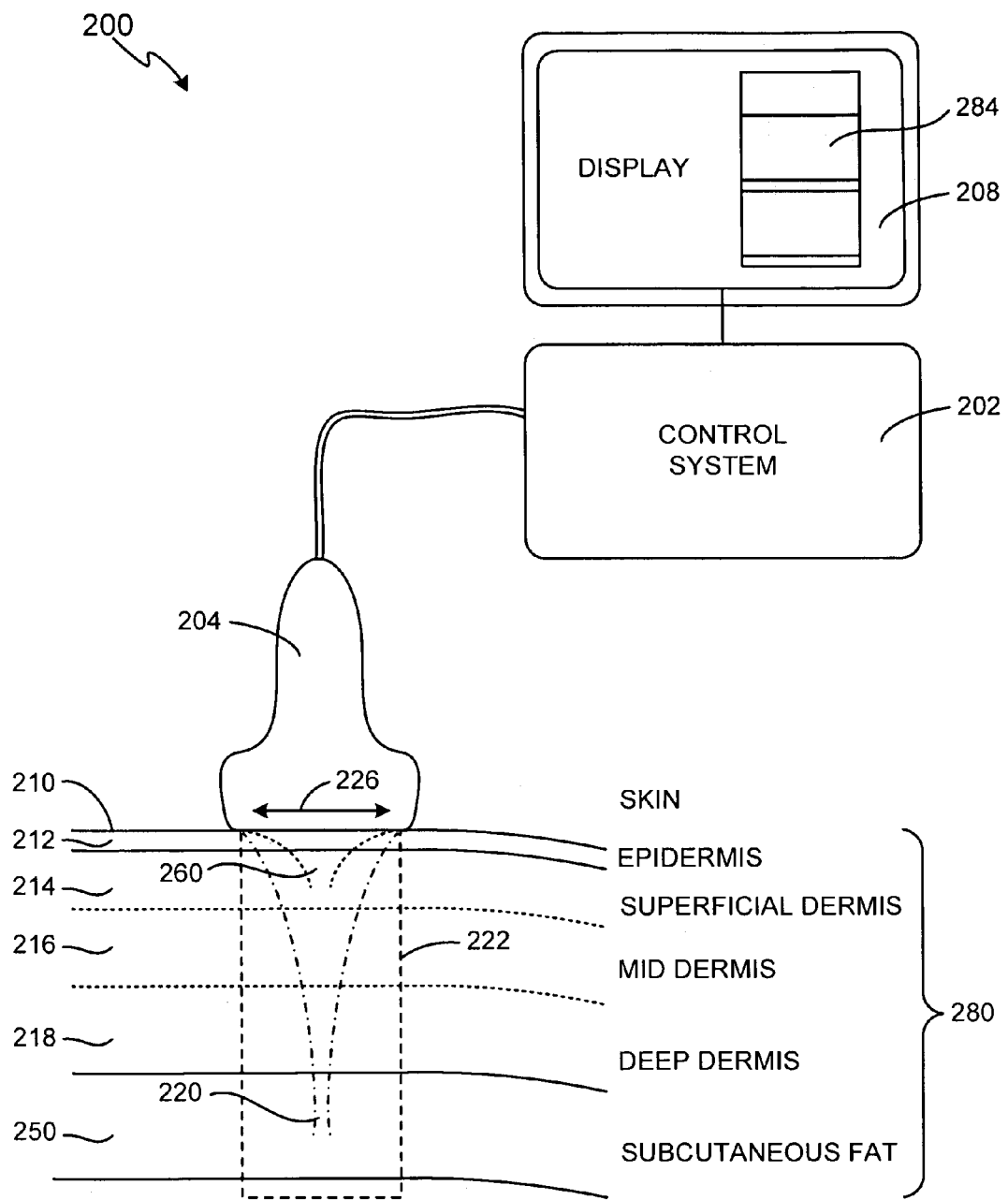

In accordance with another exemplary embodiment, with reference to FIG. 2D, an expanded region of interest 280 can suitably include a combination of tissues, such as subcutaneous fat/adipose tissue 250. A combination of such tissues includes at least one of epidermis 212, superficial dermis 214, mid dermis 216, or deep dermis 218, in combination with at least one of muscle tissue, adipose tissue, or other tissues useful for treatment. For example, treatment 260 of superficial dermis may be performed in combination with treatment 220 of subcutaneous fat 250 by suitable adjustment of the spatial and temporal parameters of transducers in probe 204.

Figure 3A:
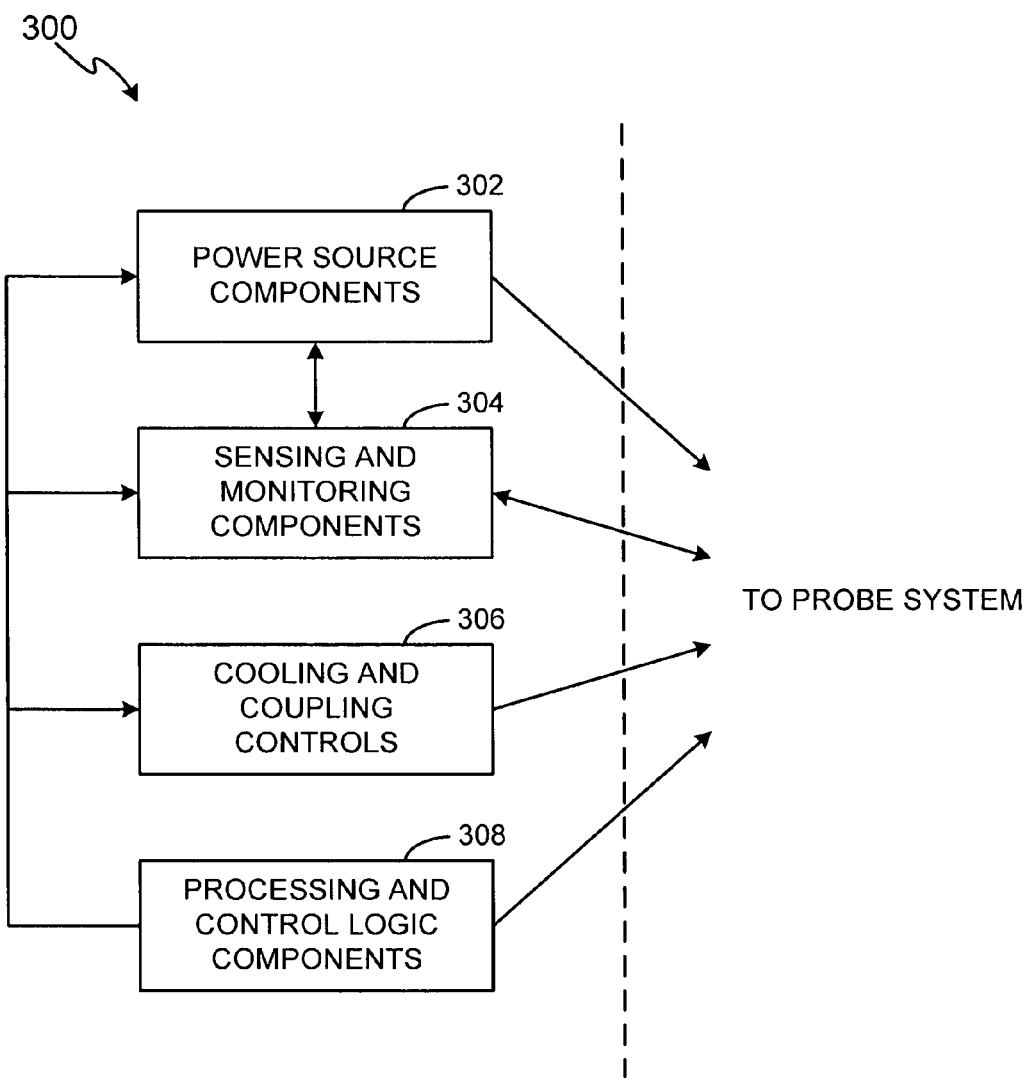
FIGS. 3A and 3B illustrate block diagrams of an exemplary control system in accordance with exemplary embodiments of the present invention.
Figure 3B:
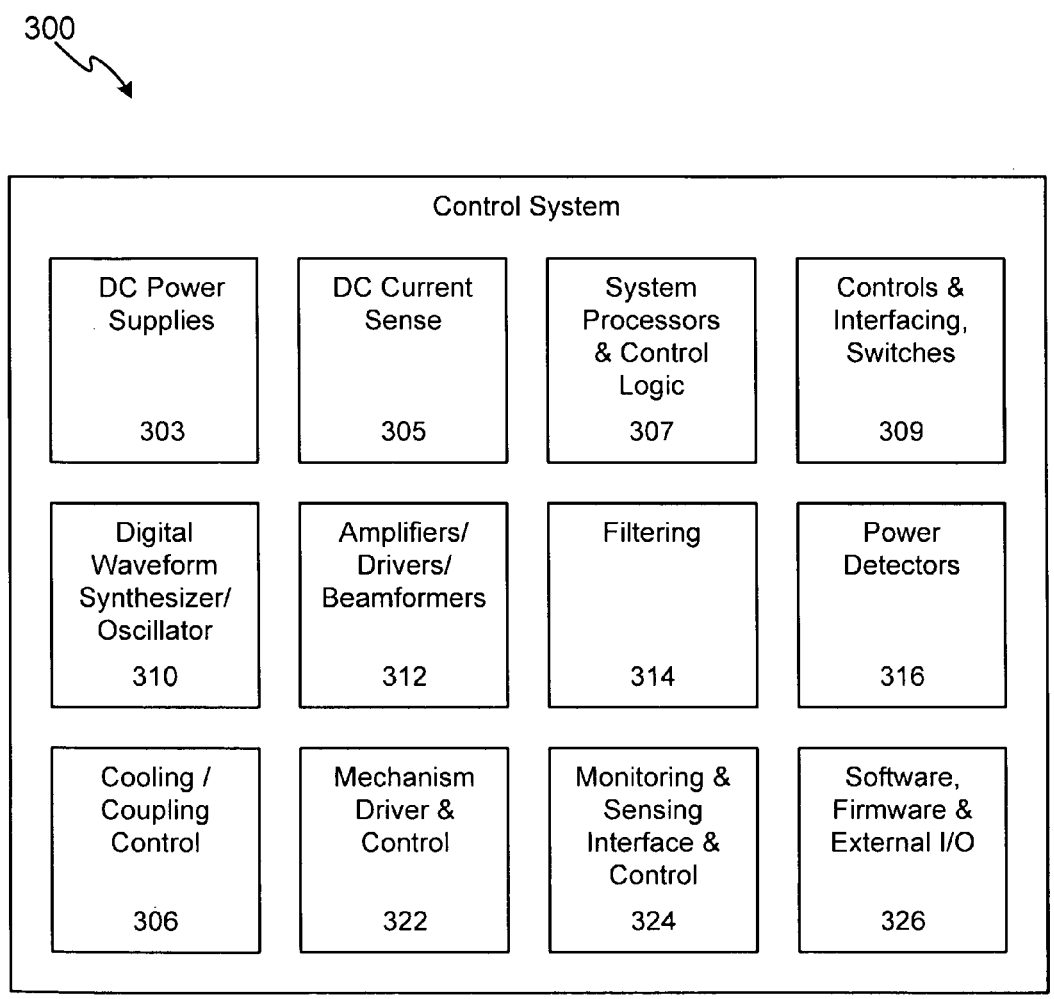

An exemplary control system 202 and display system 208 may be configured in various manners for controlling probe and system functionality for providing the various exemplary treatment methods illustrated above. For example, with reference to FIGS. 3A and 3B, in accordance with exemplary embodiments, an exemplary control system 300 can be configured for coordination and control of the entire therapeutic treatment process for producing arrays of sub-millimeter and larger zones of thermal ablation to treat the epidermal, superficial dermal, mid-dermal and deep dermal components of photoaged tissue. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury of photoaged tissue, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
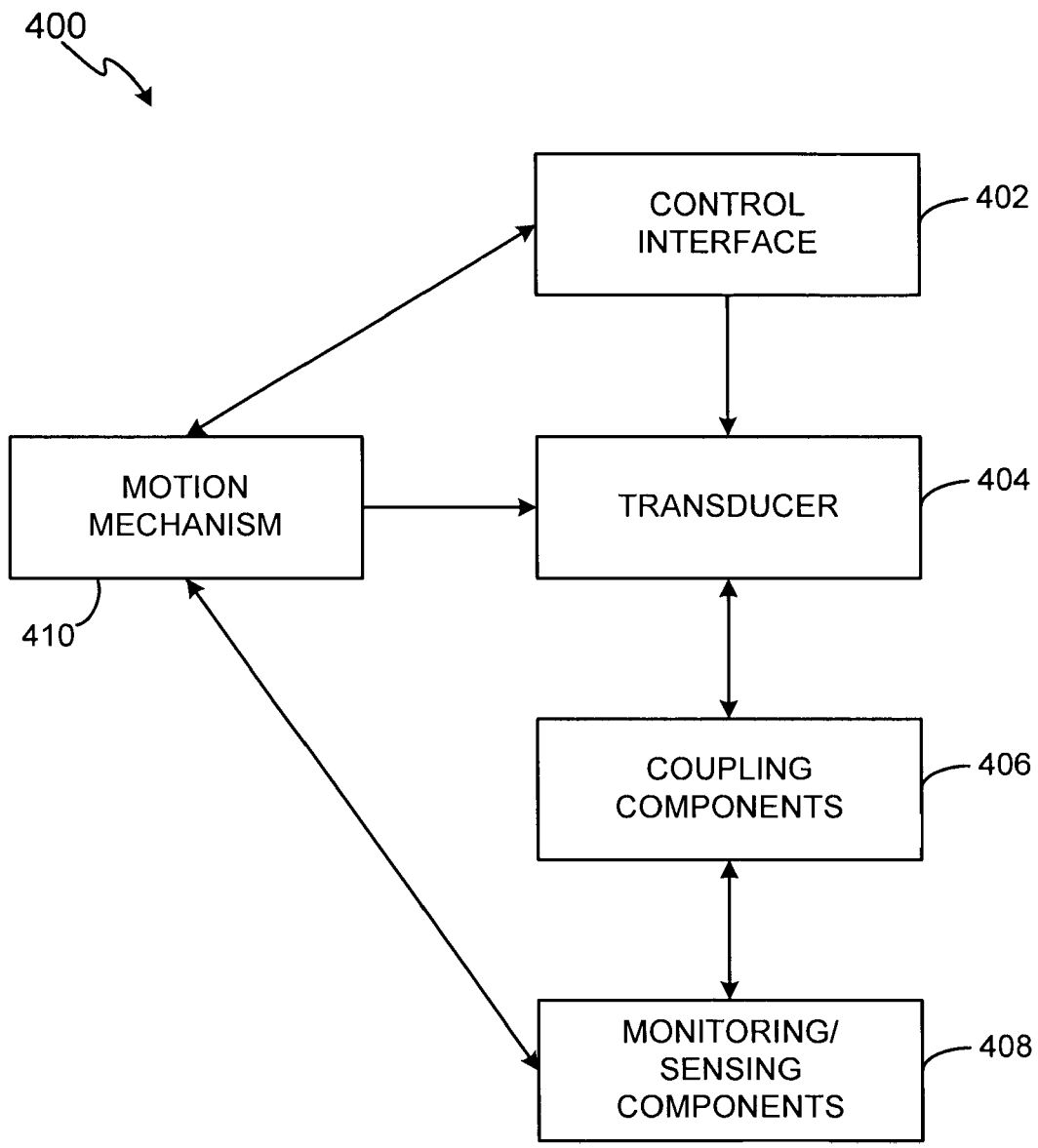
FIGS. 4A and 4B illustrate block diagrams of an exemplary probe system in accordance with exemplary embodiments of the present invention.
Figure 4B:
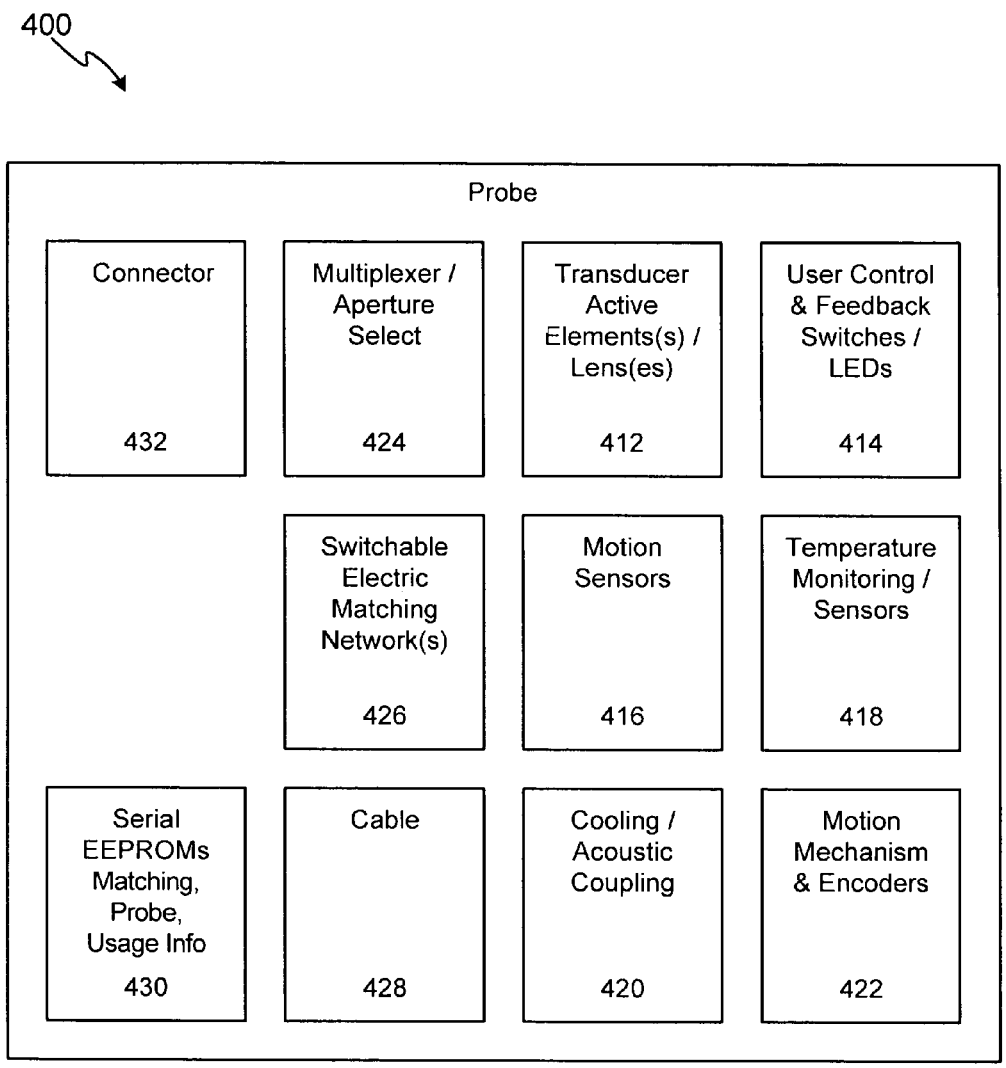

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide ultrasound energy for controlled thermal injury of photoaged tissue, and the embodiments in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or deeper region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy delivery control of transducer probe 400.

Figure 11:
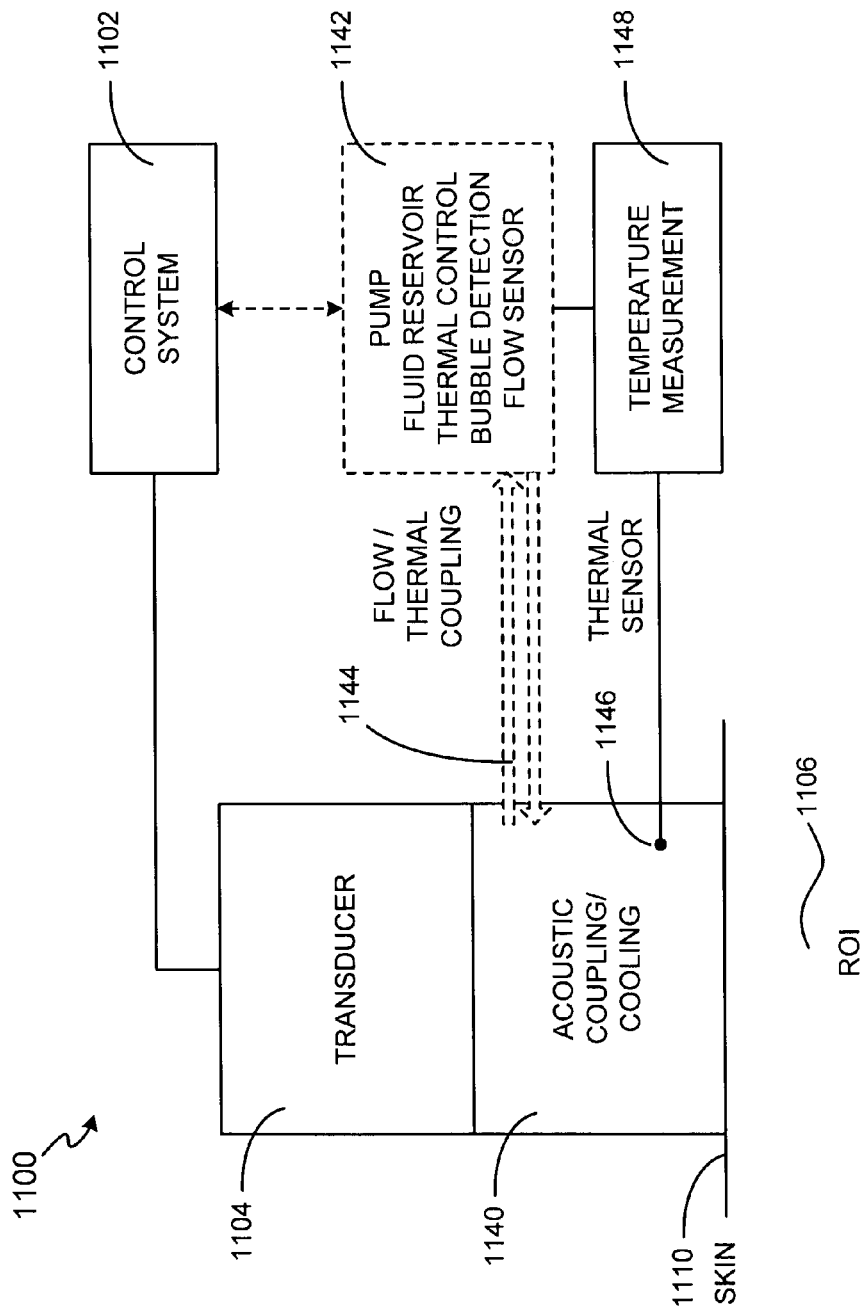
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1102, to provide thermal control at the probe to region-of-interest interface 1110 and deeper into tissue, and to remove potential waste heat from the transducer probe at region 1144. Temperature monitoring can be provided at the coupling interface via a thermal sensor 1146 to provide a mechanism of temperature measurement 1148 and control via control system 1106 and a thermal control system 1142. Thermal control may consist of passive cooling such as via heat sinks or natural conduction and convection or via active cooling such as with peltier thermoelectric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism 422 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of SMAS layers and targeted regions. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 50 MHz, and typically between 2 MHz and 25 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
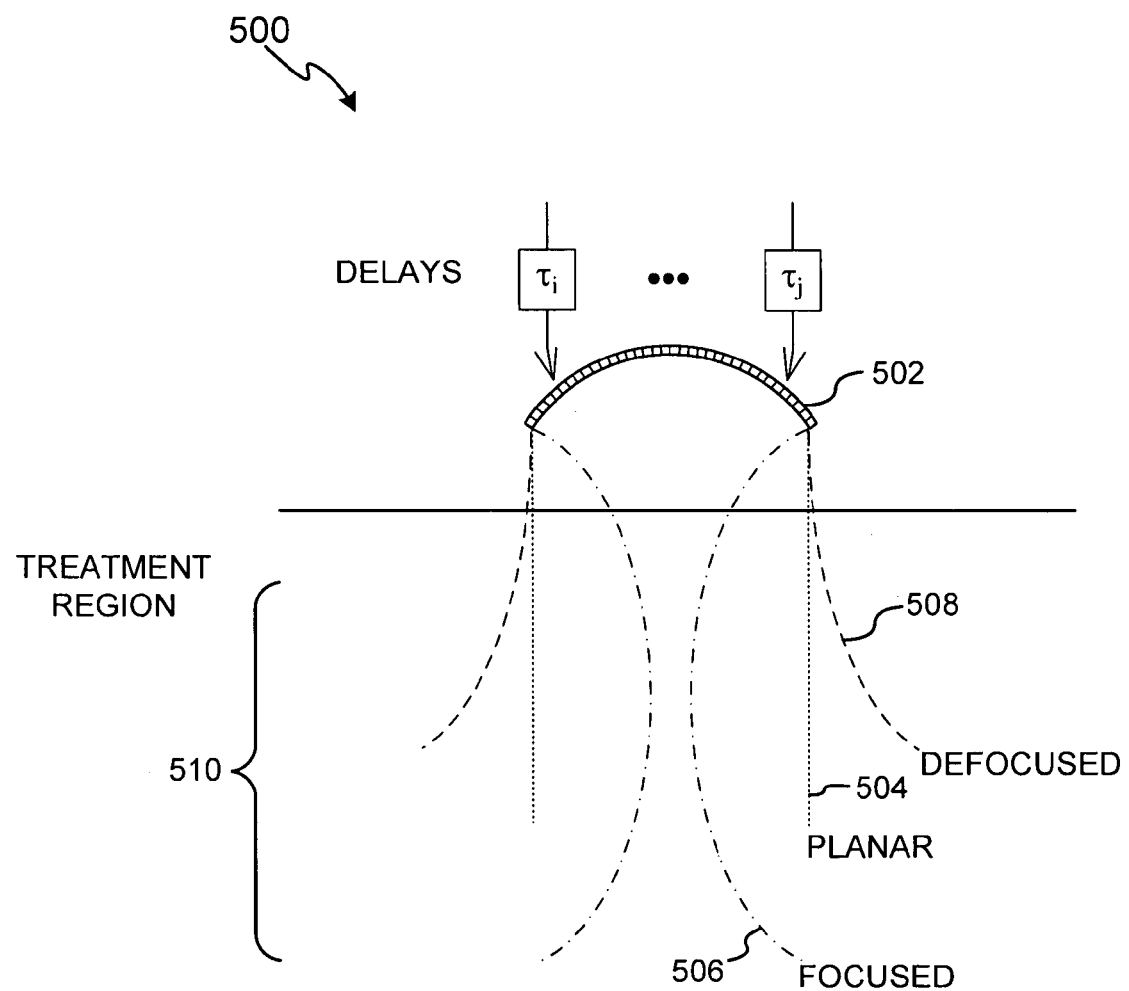
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulse-echo imaging, as disclosed in U.S. patent application Ser. No. 10/944,499, entitled "Method and System for Ultrasound Treatment with a Multi-directional Transducer", filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and or defocus the sound field. For example, with reference to exemplary embodiments depicted in FIGS. 6A and 6B, transducer 600 may also be configured with an electronic focusing array 604 in combination with one or more transduction elements 606 to facilitate increased flexibility in treating ROI 610. Array 604 may be configured in a manner similar to transducer 502. That is, array 604 can be configured as an array of electronic apertures that may be operated by a variety of phases via variable electronic time delays, for example, $T_1, T_2 \ldots T_j$. By the term "operated," the electronic apertures of array 604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 [A] are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
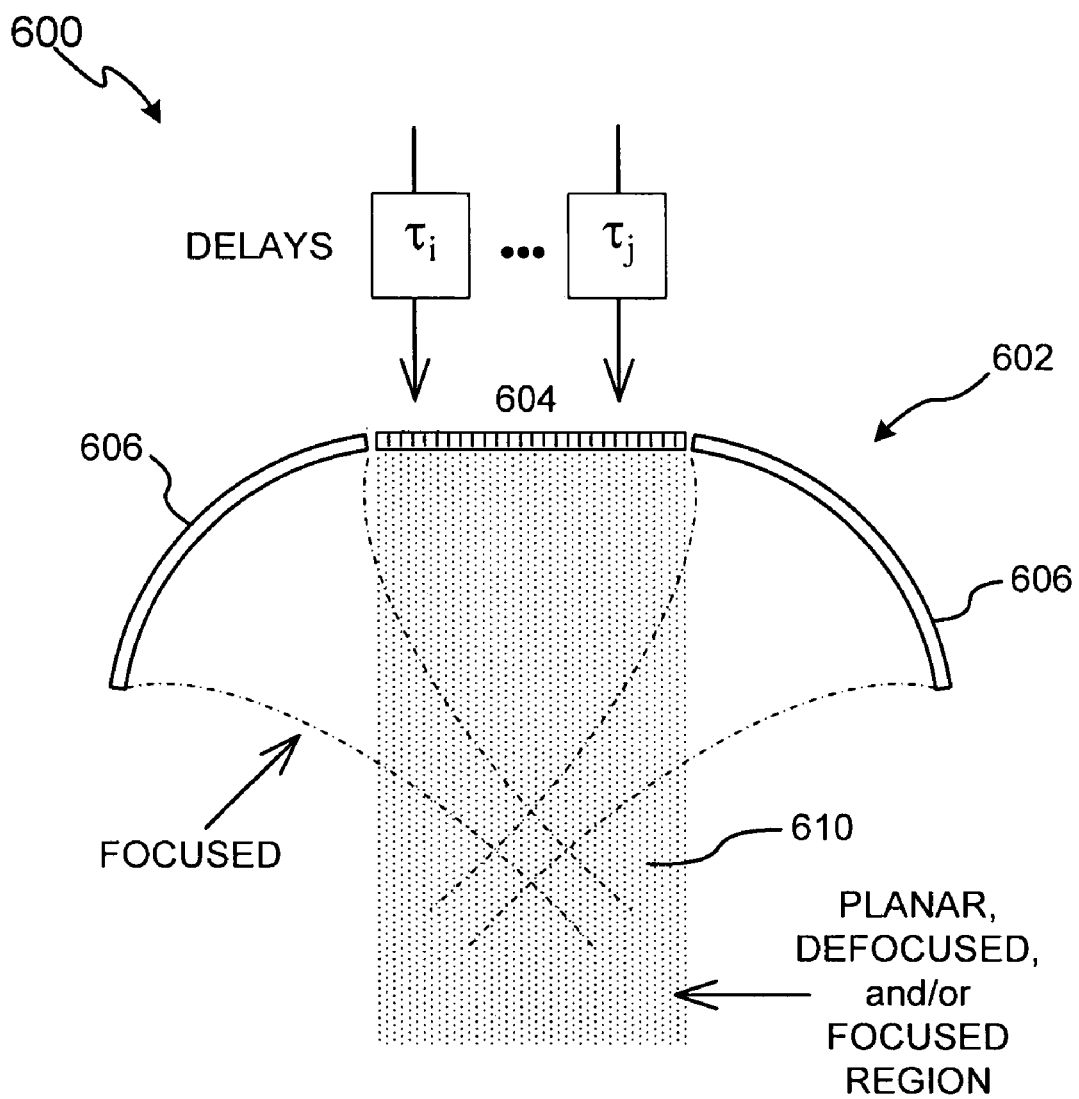
FIGS. 6A and 6B illustrate cross-sectional diagrams of an exemplary transducer in accordance with exemplary embodiments of the present invention.
Figure 6B:
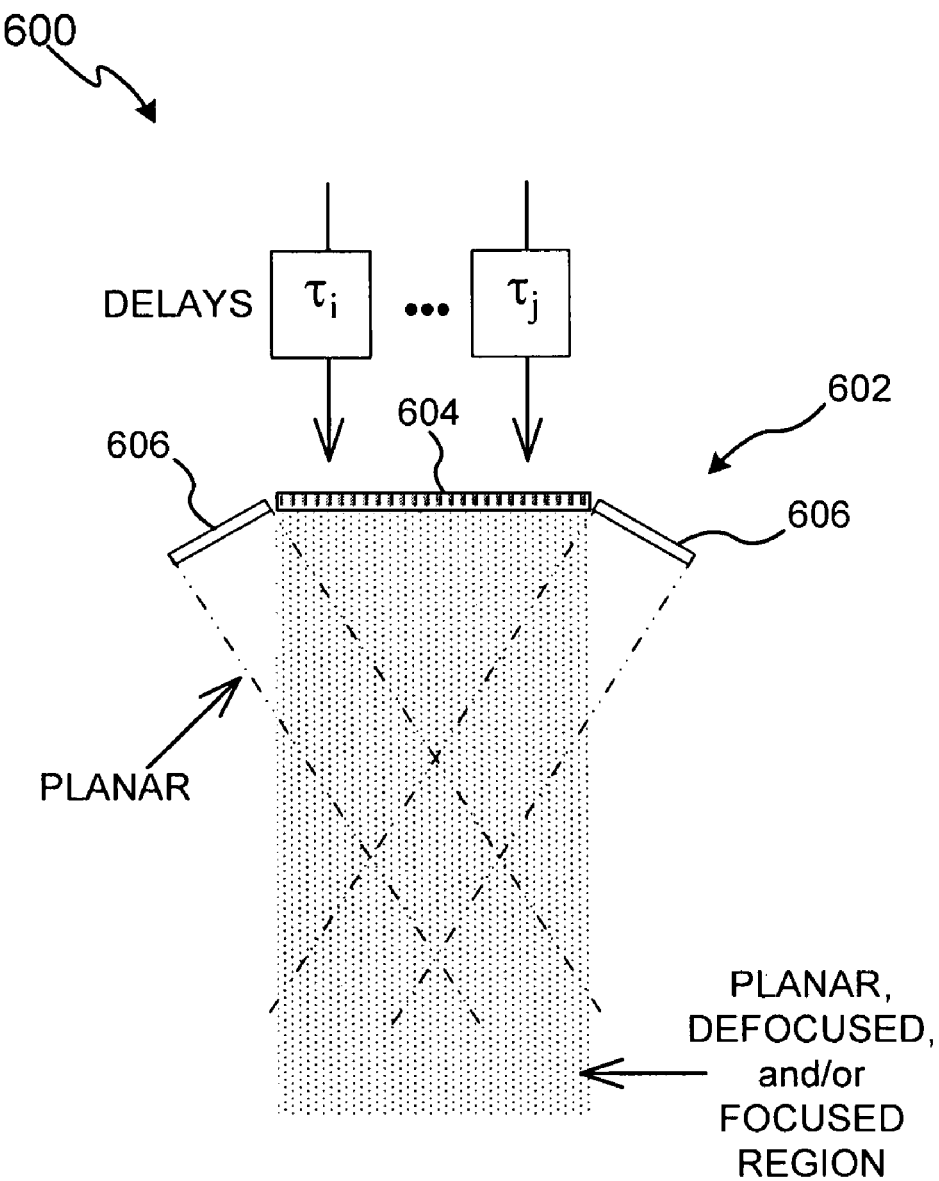

In another exemplary embodiment, depicted in FIG. 6B, transduction elements 606[B] can be configured to be substantially flat in order to provide substantially uniform energy to ROI 610. While FIGS. 6A and 6B depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
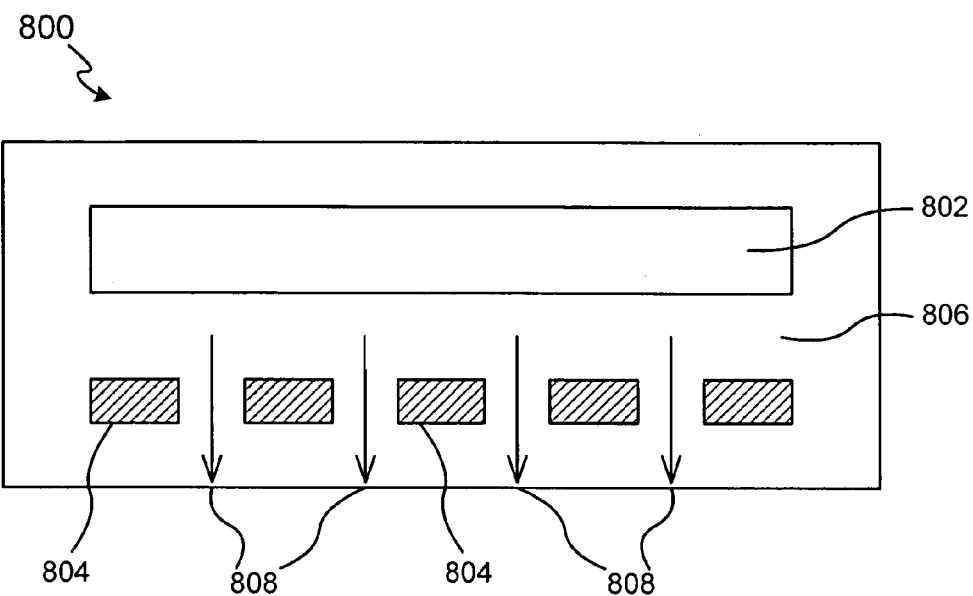
FIGS. 8A and 8B illustrate cross-sectional diagrams of an exemplary transducer in accordance with another exemplary embodiment of the present invention.
Figure 8B:
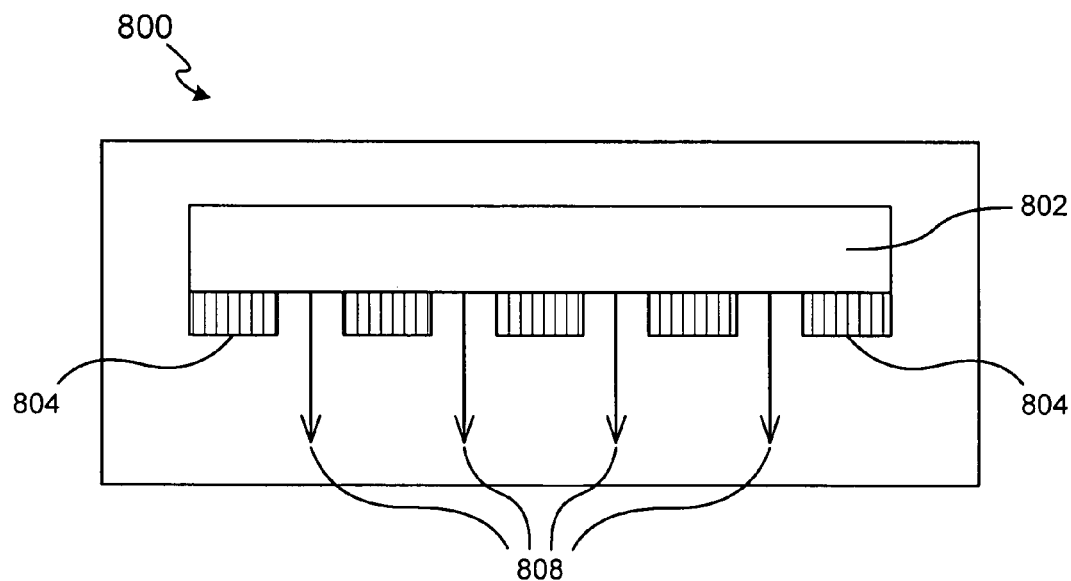

With reference to FIGS. 8A and 8B, transducer 404 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
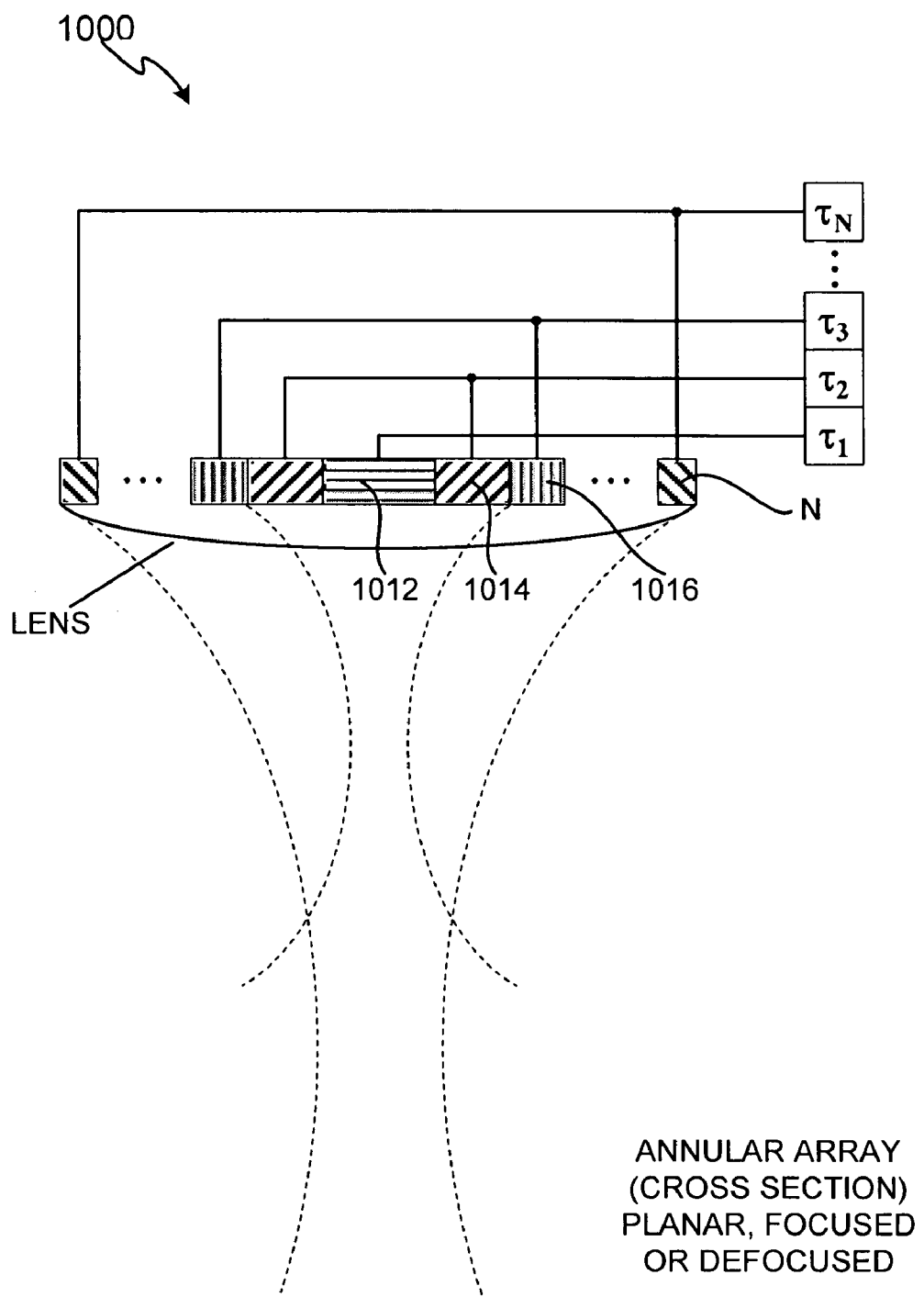
FIGS. 10A-10F illustrate cross-sectional diagrams of exemplary transducers in accordance with other exemplary embodiments of the present invention.
Figure 10B:
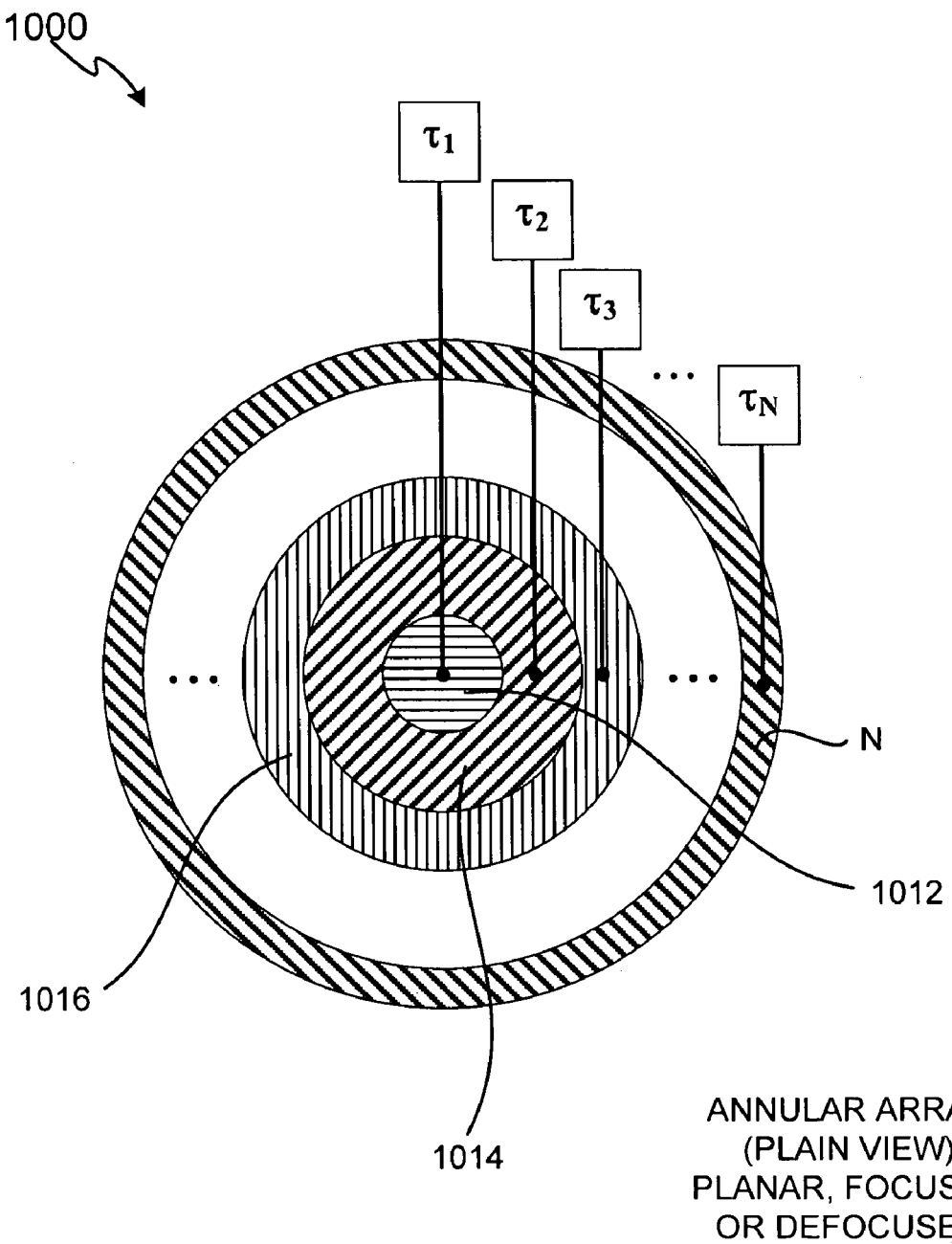
Figure 10C:
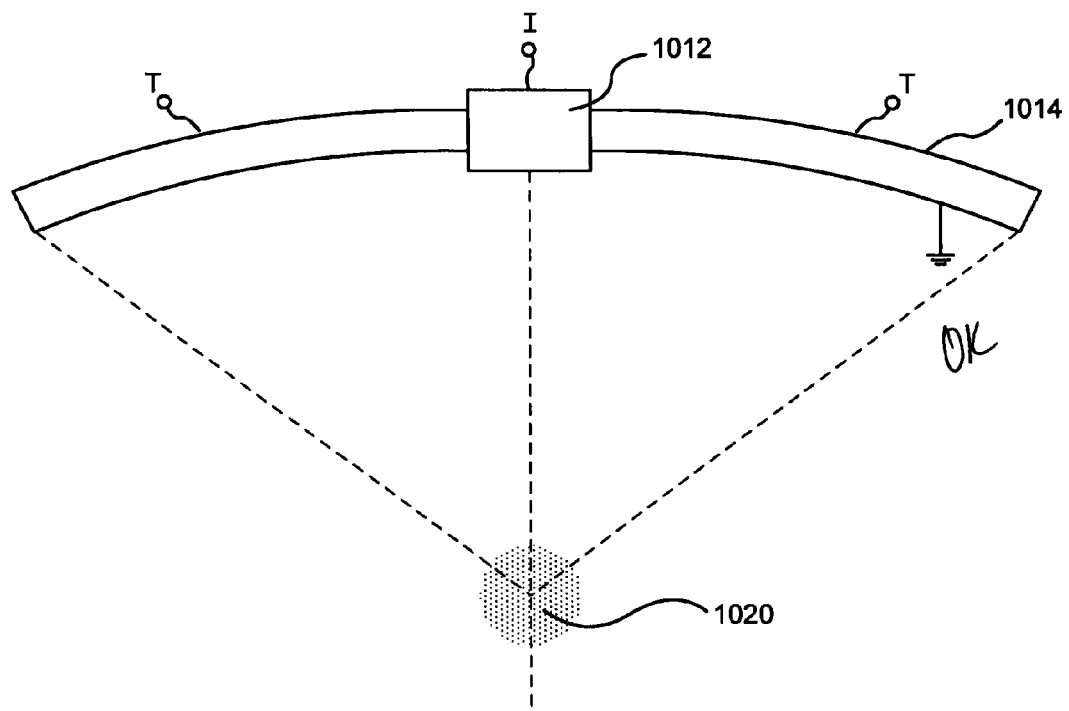
Figure 10D:
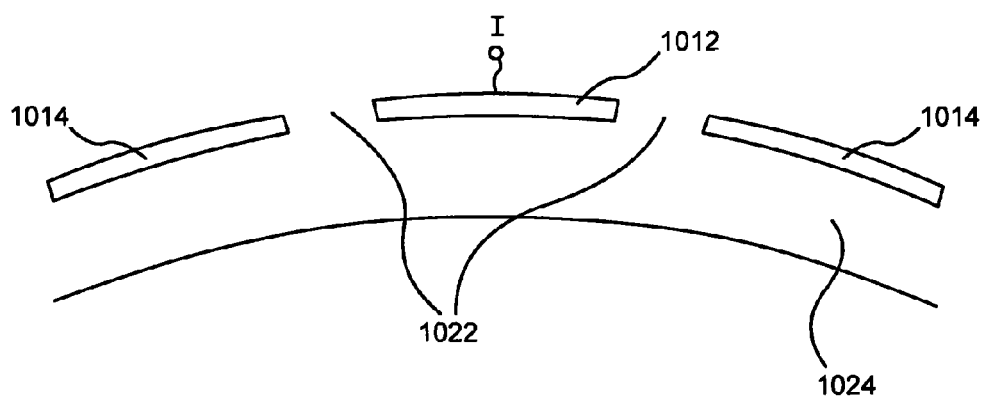
Figure 10E:
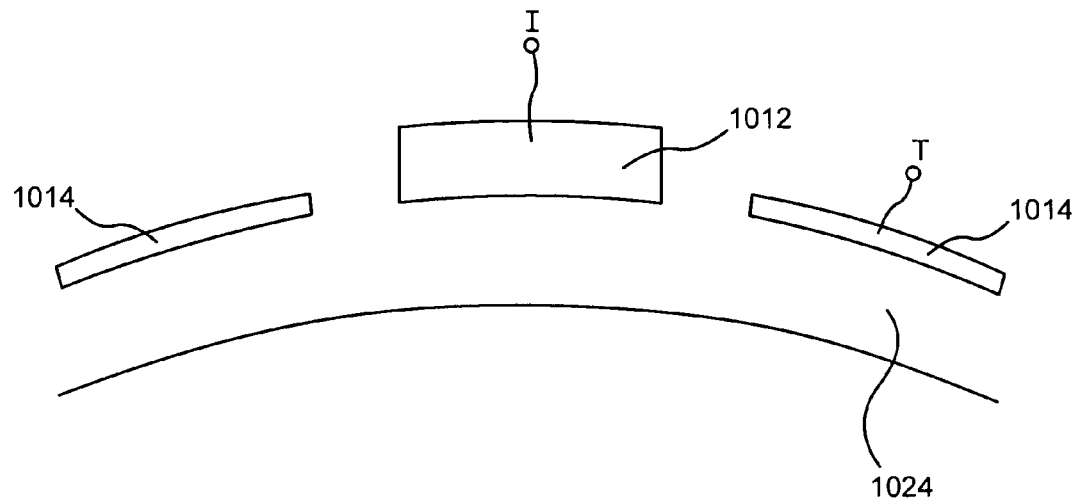

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, $\tau_1, \tau_2, \tau_3 \ldots \tau_N$. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 800 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

Figure 9:
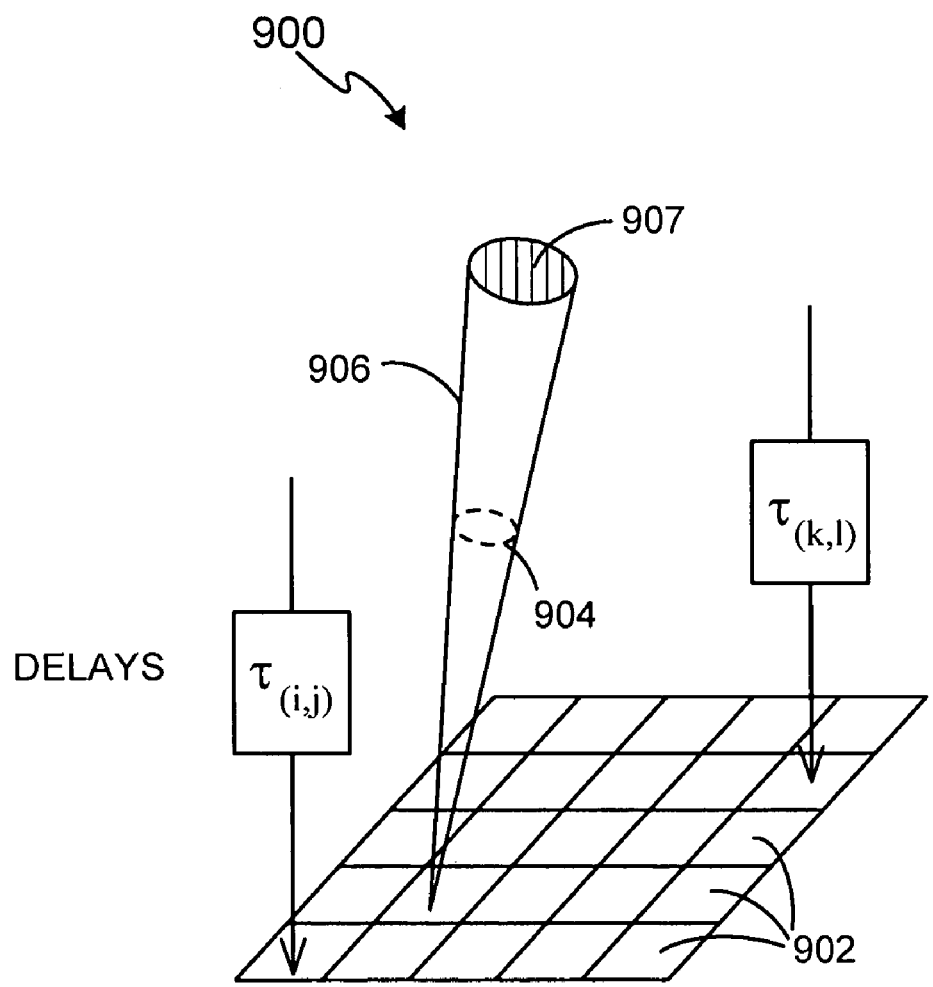
FIG. 9 illustrates an exemplary transducer configured as a two-dimensional array for ultrasound treatment in accordance with an exemplary embodiment of the present invention.

In accordance with another exemplary embodiment, transducer probe 400 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide-three dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
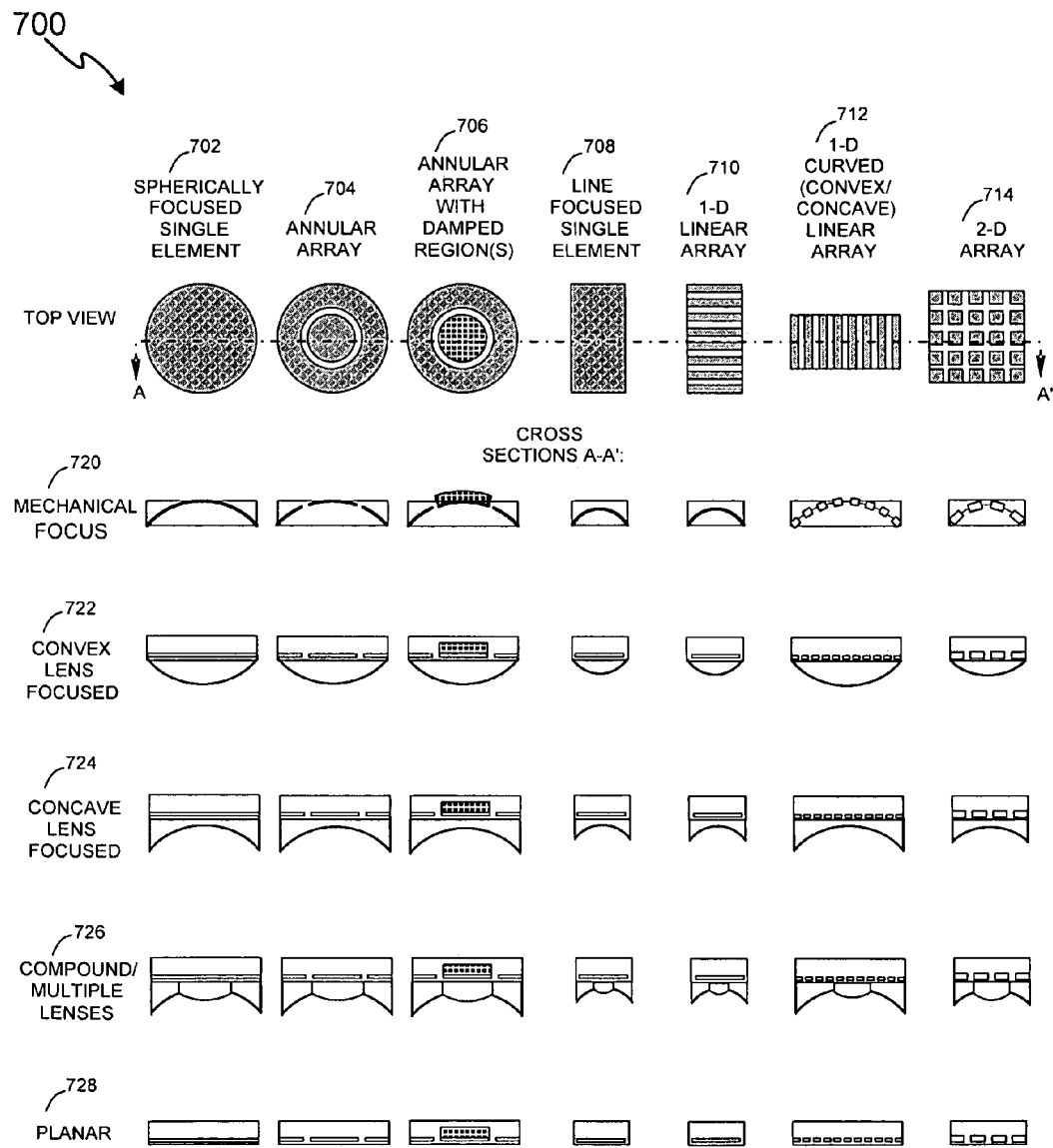
FIG. 7 illustrates exemplary transducer configurations for ultrasound treatment in accordance with various exemplary embodiments of the present invention.
Figure 10F:
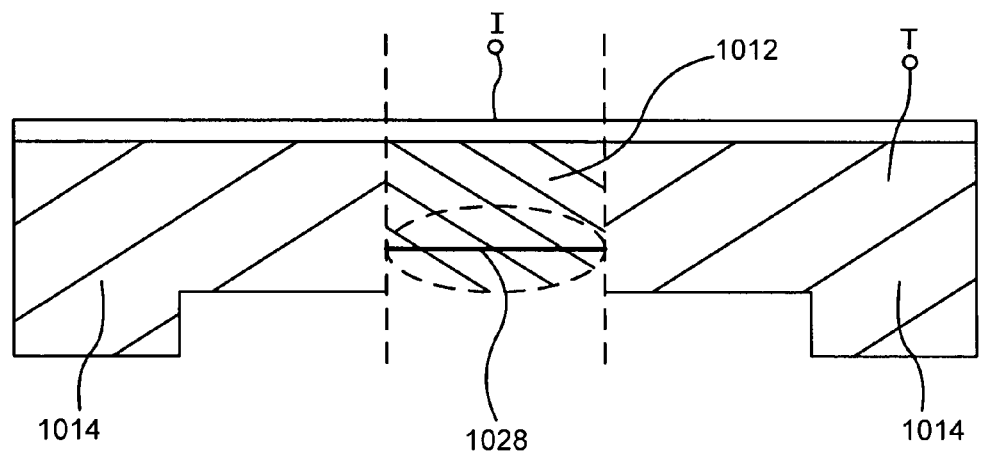

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-D linear arrays 710, 1-D curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIGS. 10C-10F.

Moreover, such transduction elements 700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy. A means of transferring energy to and from the transducer to the region of interest is provided.

Figure 12:
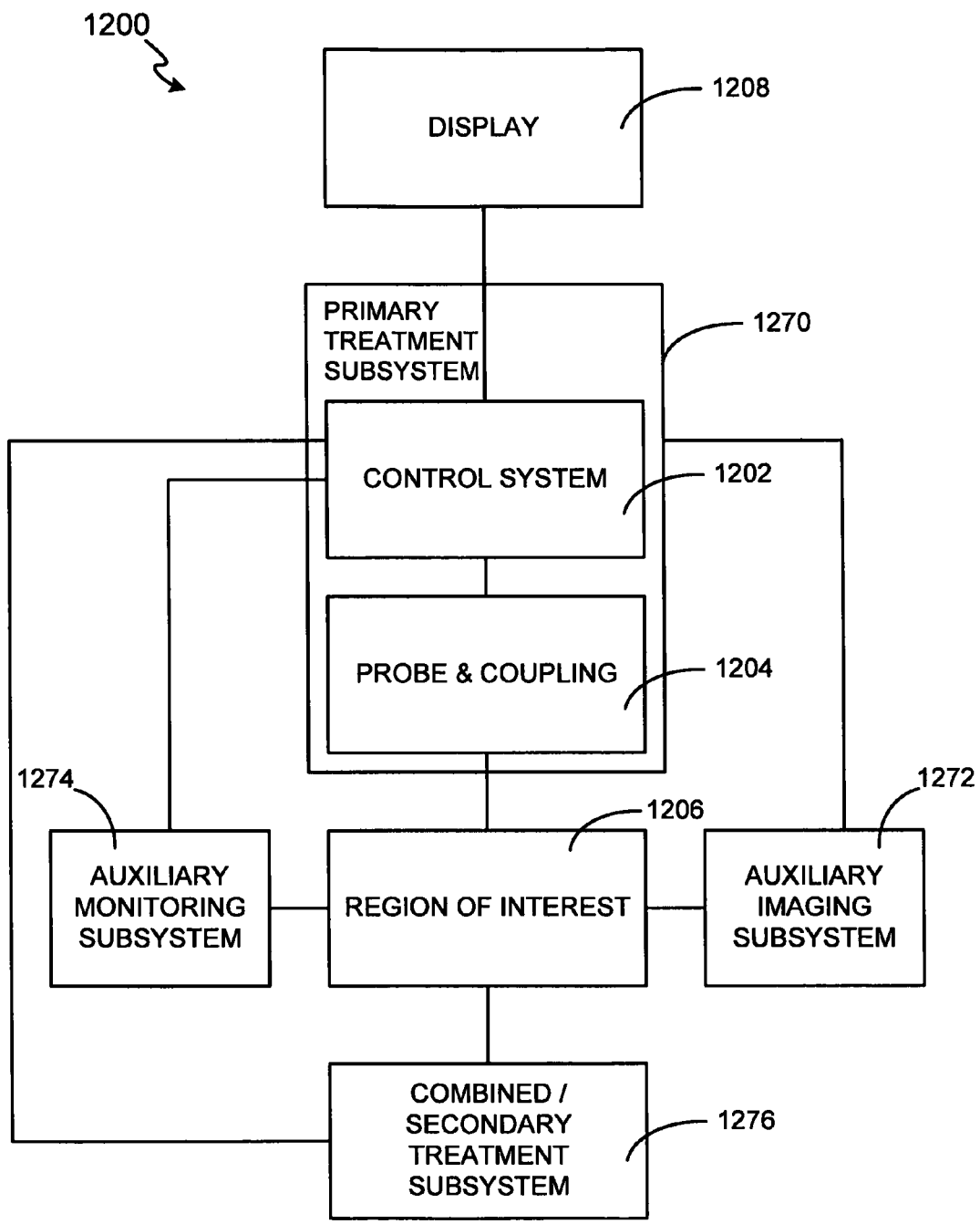
FIG. 12 illustrates a block diagram of an ultrasound treatment system combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treating a region of interest 1202 can comprise a control system 1206, a probe 1204, and a display 1208. Treatment system 1200 further comprises an auxiliary imaging modality 1274 and/or auxiliary monitoring modality 1272 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of region-of-interest 1202, including imaging/monitoring enhancements. Such imaging/monitoring enhancement for ultrasound imaging via probe 1204 and control system 1206 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF), intense pulsed light (IPL), laser, infrared laser, microwave, or any other suitable energy source.

Figure 13:
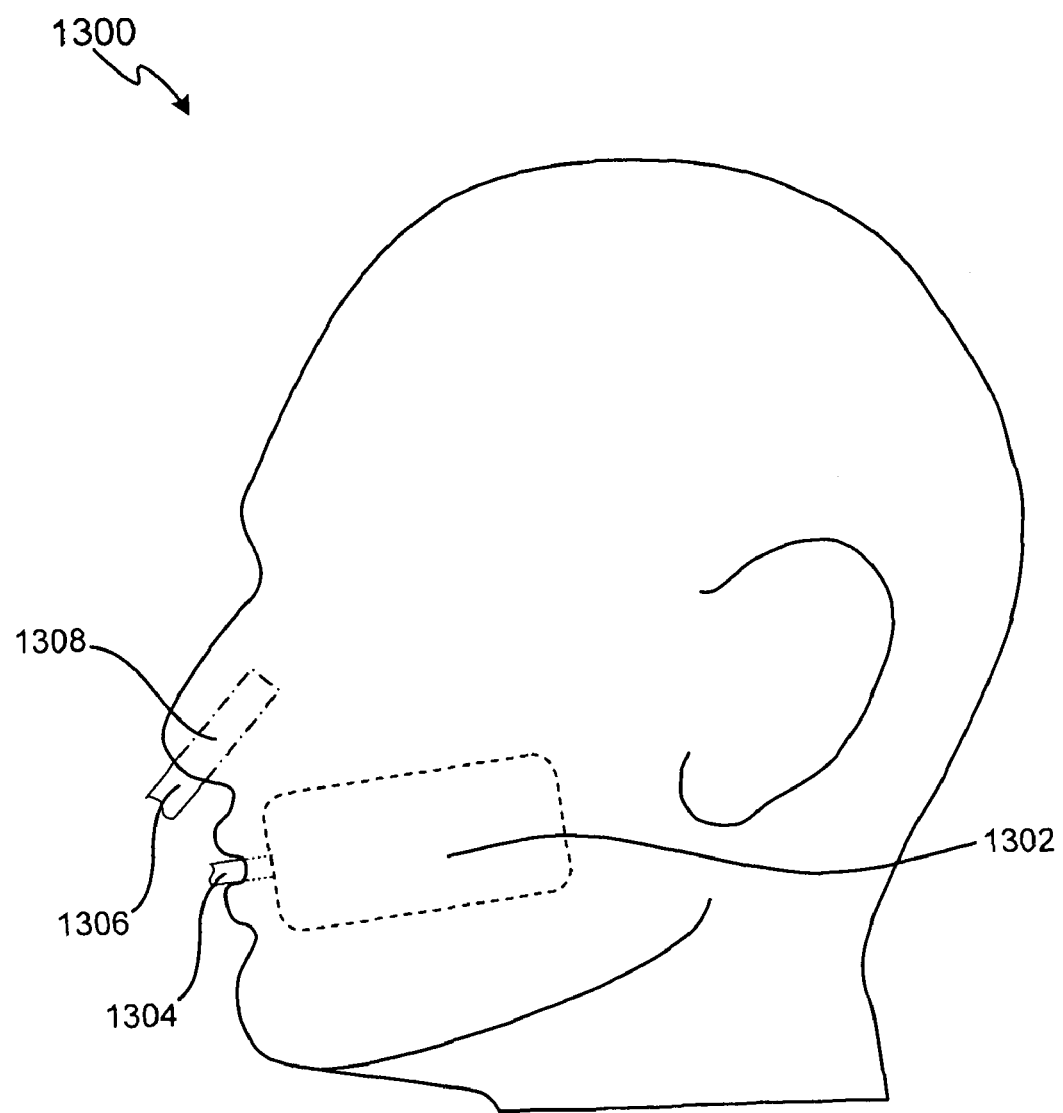
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest 1302 and/or 1308 may be aided, augmented, and/or delivered with passive or active devices 1304 and/or 1306 within the oral and/or nasal cavity, respectively. For example, if passive or active device 1304 and/or 1306 are second transducers or acoustic reflectors acoustically coupled to the mucous membranes it is possible to obtain through transmission, tomographic, or round-trip acoustic waves which are useful for treatment monitoring, such as in measuring acoustic speed of sound and attenuation, which are temperature dependent; furthermore such transducers could be used to treat and/or image. In addition an active, passive, or active/passive object 1304 and/or 1306 may be used to flatten the skin, and/or may be used as an imaging grid, marker, or beacon, to aid determination of position. A passive or active device 1304 and/or 1306 may also be used to aid cooling or temperature control. Natural air in the oral cavity and/or nasal cavity may also be used as passive device 1304 and/or 1306 whereby it may be utilized to as an acoustic reflector to aid thickness measurement and monitoring function.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

What is claimed is:

1. A method for providing treatment of photoaged tissue, said method comprising:
   imaging a region of interest below a tissue surface with an imaging and therapy transducer;
   targeting said region of interest below a tissue surface and comprising at least two of epidermal, superficial dermal, mid-dermal and deep dermal tissues;
   adjusting to a depth in said region of interest based on said imaging;
   delivering ablative ultrasound energy from said imaging and therapy transducer to said depth within said region of interest;
   creating a conformal lesion in at least two of said epidermal, superficial dermal, mid-dermal and deep dermal tissues;
   coagulating a portion of said region of interest; and
   monitoring for rejuvenation of said tissue surface.

2. The method of claim 1, wherein said delivering ablative ultrasound energy comprises producing arrays of sub-millimeter and larger zones of thermal ablation within at least two of said epidermal, superficial dermal, mid-dermal and deep dermal tissues.

3. The method of claim 2, wherein said producing arrays of sub-millimeter and larger zones of thermal ablation comprises scanning said transducer along a line above said photoaged tissue to produce a matrix of spaced treatment spots.

4. The method of claim 3, wherein said producing of a matrix of spaced treatment spots comprises adjusting of treatment depths within said region of interest.

5. The method of claim 1, wherein said targeting comprises adjustment of spatial and temporal parameters based on imaging of at least two of said epidermal, superficial dermal, mid-dermal and deep dermal tissue locations.

6. The method of claim 1, wherein said monitoring for rejuvenation of said tissue surface comprises measurement of results of treatment of at least two of said epidermal, superficial dermal, mid-dermal and deep dermal tissue as imaged during and after said of delivering ablative ultrasound energy.

7. The method of claim 1, wherein said imaging a region of interest below a tissue surface comprises generating three-dimensional imaging information.

8. The method of claim 1, wherein said targeting comprises targeting a three-dimensional treatment region.

9. The method of claim 1, wherein said delivering ablative energy further comprises cooling through tissue regions comprising said at least two of epidermal, superficial dermal, mid-dermal and deep dermal tissue to facilitate treatment.

10. A method of rejuvenating photoaged skin on a subject, the method comprising:
    imaging a treatment area comprising a photoaged skin surface and at least two of epidermal tissue, superficial dermal tissue, mid-dermal tissue and deep dermal tissues;
    targeting a depth in said treatment area comprising a photoaged skin surface and at least two of epidermal tissue, superficial dermal, mid-dermal tissue, and deep dermal tissue;
    adjusting to said depth based on said imaging;
    delivering ultrasound energy to said treatment area at said depth below said photoaged skin surface;
    creating a conformal lesion in a portion of said at least two of epidermal tissue, superficial dermal tissue, mid-dermal tissue, and deep dermal tissue; and
    causing shrinkage of said at least two of epidermal tissue, superficial dermal tissue, mid-dermal tissue, and deep dermal tissue, thereby rejuvenating said photoaged skin surface.

11. The method of claim 10 further comprising controlling at least one of a spatial parameter and a temporal parameter of said ultrasound energy.

12. The method of claim 10 further comprising re-imaging said treatment area after the step of said causing shrinkage of said at least two of epidermal tissue, superficial dermal tissue, mid-dermal tissue, and deep dermal tissue.

13. The method of claim 10 further comprising producing an array of conformal lesions in a said portion of said at least two of epidermal tissue, superficial dermal tissue, mid-dermal tissue, and deep dermal tissue.

14. The method of claim 10 further comprising moving said ultrasound energy.

15. The method of claim 14 further comprising causing shrinkage at a second depth in said at least two of epidermal tissue, superficial dermal tissue, mid-dermal tissue, and deep dermal tissue.

16. A method of treating photoaged skin, the method comprising:

targeting a portion of a treatment area comprising a photoaged skin surface and at least two of epidermal tissue, superficial dermal tissue, mid-dermal tissue, and deep dermal tissue;

delivering ultrasound energy to said treatment area at a first depth below said photoaged skin surface;

moving said delivering ultrasound energy to said treatment area at a second depth below said photoaged skin surface;

creating a plurality of conformal lesions in said at least two of epidermal tissue, superficial dermal tissue, mid-dermal tissue, and deep dermal tissue; and coagulating a portion of said at least two of epidermal tissue, superficial dermal tissue, mid-dermal tissue, and deep dermal tissue, thereby rejuvenating said photoaged skin surface.

17. The method of claim 16 further comprising imaging said treatment area comprising said photoaged skin surface and at least two of epidermal, superficial dermal tissue, mid-dermal and deep dermal tissue.

18. The method of claim 17 further comprising re-imaging said treatment area after the step of said coagulating a portion of said at least two of epidermal tissue, superficial dermal tissue, mid-dermal tissue, and deep dermal tissue.

19. The method of claim 16 further comprising controlling at least one of a spatial parameter and a temporal parameter of said ultrasound energy.

20. The method of claim 16 further comprising producing an array of conformal lesions in a portion of said at least two of epidermal tissue, superficial dermal tissue, mid-dermal tissue, and deep dermal tissue.

21. The method of claim 16 further comprising coagulating a second portion of said at least two of epidermal tissue, superficial dermal tissue, mid-dermal tissue, and deep dermal tissue.

* * * * *